(12) United States Patent
Giguere et al.

(10) Patent No.: US 9,309,258 B2
(45) Date of Patent: *Apr. 12, 2016

(54) PROCESS FOR N-DEALKYLATION OF TERTIARY AMINES

(71) Applicant: Rhodes Technologies, Coventry, RI (US)

(72) Inventors: Joshua Robert Giguere, Sharon, MA (US); Helge Alfred Reisch, Westerly, RI (US); Sergio Sandoval, West Warwick, RI (US); Jake Larry Stymiest, Foster, RI (US)

(73) Assignee: Rhodes Technologies, Coventry, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/558,513

(22) Filed: Dec. 2, 2014

(65) Prior Publication Data

US 2015/0087839 A1    Mar. 26, 2015

Related U.S. Application Data

(63) Continuation of application No. 13/711,288, filed on Dec. 11, 2012, now Pat. No. 8,921,556, which is a continuation of application No. PCT/IB2011/001328, filed on Jun. 10, 2011.

(60) Provisional application No. 61/354,017, filed on Jun. 11, 2010.

(51) Int. Cl.
  *C07D 471/02* (2006.01)
  *C07D 489/12* (2006.01)
  *C07D 489/08* (2006.01)
  *C07D 489/02* (2006.01)

(52) U.S. Cl.
  CPC ............ *C07D 489/12* (2013.01); *C07D 489/02* (2013.01); *C07D 489/08* (2013.01)

(58) Field of Classification Search
  None
  See application file for complete search history.

(56) References Cited

U.S. PATENT DOCUMENTS

| | | |
|---|---|---|
| 1,468,805 A | 9/1923 | Freund et al. |
| 1,485,673 A | 3/1924 | Freund et al. |
| 2,191,786 A | 2/1940 | Aronow |
| 2,583,420 A | 1/1952 | Garber et al. |
| 2,772,270 A | 11/1956 | Weiss |
| 2,806,033 A | 9/1957 | Mozes et al. |
| 3,254,088 A | 5/1966 | Lewenstein et al. |
| 3,332,950 A | 7/1967 | Blumberg et al. |
| 3,342,824 A | 9/1967 | Pohland et al. |
| 3,355,486 A | 11/1967 | Berkowitz et al. |
| 3,433,791 A | 3/1969 | Bentley et al. |
| 3,749,646 A | 7/1973 | Pirt |
| 3,812,132 A | 5/1974 | Robertson |
| 3,872,127 A | 3/1975 | Merz et al. |
| 3,905,981 A | 9/1975 | Olofson et al. |
| 3,923,987 A | 12/1975 | Merz et al. |
| 3,931,187 A | 1/1976 | Langbein |
| 4,003,903 A | 1/1977 | Schwartz |
| 4,045,440 A | 8/1977 | Rapoport |
| 4,141,897 A | 2/1979 | Olofson et al. |
| 4,217,287 A | 8/1980 | Bozik et al. |
| 4,217,787 A | 8/1980 | Liebing et al. |
| 4,236,008 A | 11/1980 | Henderson |
| 4,472,253 A | 9/1984 | Schwartz |
| 4,639,520 A | 1/1987 | Kavka |
| 4,667,037 A | 5/1987 | Bryant |
| 4,795,813 A | 1/1989 | Schwartz |
| 5,112,975 A | 5/1992 | Wallace |
| 5,668,285 A | 9/1997 | Rice et al. |
| 5,847,142 A | 12/1998 | Mudryk et al. |
| 5,869,669 A | 2/1999 | Huang et al. |
| 5,880,294 A | 3/1999 | Nomura et al. |
| 5,922,876 A | 7/1999 | Huang et al. |
| 5,952,495 A | 9/1999 | Huang et al. |
| 5,994,372 A | 11/1999 | Yaksh |
| 6,067,749 A | 5/2000 | Fist et al. |
| 6,177,567 B1 | 1/2001 | Chiu et al. |
| 6,262,266 B1 | 7/2001 | Chiu et al. |
| 6,277,859 B1 | 8/2001 | Nagase et al. |
| 6,291,675 B1 | 9/2001 | Coop et al. |
| 6,335,459 B1 | 1/2002 | Lopez-Tapia et al. |
| 6,365,742 B1 | 4/2002 | Mudryk et al. |
| 6,376,211 B1 | 4/2002 | Little et al. |
| 6,395,900 B1 | 5/2002 | Coop et al. |
| 6,403,798 B2 | 6/2002 | Chiu et al. |

(Continued)

FOREIGN PATENT DOCUMENTS

| | | |
|---|---|---|
| CA | 1244825 | 11/1988 |
| EP | 0632041 | 1/1995 |

(Continued)

OTHER PUBLICATIONS

Abdel-Monem et al. (1972) *J. Med. Chem.* 15(2):208-210.
Acosta et al. (1994) *J. Chem. Soc., Chem. Commun.* 17(7):1985-1986.
Aggarwal et al. (2003) *Org. Lett.* 5(23):4417-4420.
Andre et al. (1992) *Synthetic Comm.* 22(16):2313-2327.
Balas et al. (2009) *J. Med. Chem.* 52:1005-1017.
Barber et al. (1975) *J. Med. Chem.* 18(11):1074-1077.
Bellingham et al. (2004) *Org. Process Res. Devel.* 8:279-282.

(Continued)

*Primary Examiner* — Heidi Reese
(74) *Attorney, Agent, or Firm* — Dechert LLP

(57) ABSTRACT

The present disclosure provides improved methods for N-dealkylation of tertiary amines, including methods for N-demethylation of alkaloids and opioids, in which the dealkylation reaction is carried out in a solvent comprising a tertiary alcohol. The present disclosure also provides improved processes for preparing semi-synthetic opioids that incorporate the disclosed methods for N-dealkylation of tertiary amines.

37 Claims, No Drawings

(56) References Cited

U.S. PATENT DOCUMENTS

| | | | |
|---|---|---|---|
| 6,405,301 B1 | 6/2002 | Duranton | |
| 6,569,170 B1 | 5/2003 | Kellogg | |
| 6,723,894 B2 | 4/2004 | Fist et al. | |
| 6,790,959 B1 | 9/2004 | Lin et al. | |
| 6,864,370 B1 | 3/2005 | Lin et al. | |
| 6,949,645 B1 | 9/2005 | Francis | |
| 6,972,332 B1 | 12/2005 | Francis | |
| 7,071,336 B2 | 7/2006 | Francis et al. | |
| 7,129,248 B2 | 10/2006 | Chapman et al. | |
| 7,217,822 B2 | 5/2007 | Comin et al. | |
| 7,285,665 B2 | 10/2007 | Cantrell et al. | |
| 7,405,301 B2 | 7/2008 | Scammells et al. | |
| 7,435,817 B2 | 10/2008 | Linders et al. | |
| 7,501,433 B2 | 3/2009 | Wu et al. | |
| 7,671,204 B2 | 3/2010 | Wang et al. | |
| 7,875,718 B2 | 1/2011 | Smith et al. | |
| 7,939,543 B2 | 5/2011 | Kupper | |
| 8,134,002 B2 | 3/2012 | Huang | |
| 8,217,175 B2 | 7/2012 | Wang et al. | |
| 8,278,344 B2 | 10/2012 | Cuny et al. | |
| 8,309,727 B2 | 11/2012 | Wang et al. | |
| 8,357,802 B2 | 1/2013 | Huang | |
| 8,546,572 B2 | 10/2013 | Patel et al. | |
| 8,669,366 B2 | 3/2014 | Wang et al. | |
| 8,921,556 B2 * | 12/2014 | Giguere et al. | 546/39 |
| 2006/0005112 A1 | 1/2006 | Lilly et al. | |
| 2006/0009497 A1 | 1/2006 | Bezencon et al. | |
| 2006/0195934 A1 | 8/2006 | Apuya et al. | |
| 2006/0236421 A1 | 10/2006 | Pennell et al. | |
| 2007/0142634 A1 | 6/2007 | Barrow et al. | |
| 2007/0199090 A1 | 8/2007 | Apuya et al. | |
| 2008/0045558 A1 | 2/2008 | Gant et al. | |
| 2008/0125592 A1 | 5/2008 | Huang | |
| 2008/0146601 A1 | 6/2008 | Dung et al. | |
| 2008/0207906 A1 | 8/2008 | Wang et al. | |
| 2008/0234306 A1 | 9/2008 | Perez et al. | |
| 2008/0262231 A1 | 10/2008 | Wang et al. | |
| 2008/0275240 A1 | 11/2008 | Wang et al. | |
| 2008/0312441 A1 | 12/2008 | Mannino et al. | |
| 2009/0005564 A1 | 1/2009 | Carroll et al. | |
| 2009/0005565 A1 | 1/2009 | Carroll et al. | |
| 2009/0047279 A1 | 2/2009 | Perez et al. | |
| 2009/0075822 A1 | 3/2009 | Cotterill | |
| 2009/0118271 A1 | 5/2009 | Umeda et al. | |
| 2009/0156815 A1 | 6/2009 | Wang et al. | |
| 2009/0156819 A1 | 6/2009 | Wang et al. | |
| 2009/0221766 A1 | 9/2009 | Cheng et al. | |
| 2009/0270624 A1 | 10/2009 | Weigl et al. | |
| 2010/0022774 A1 | 1/2010 | Kvernenes et al. | |
| 2010/0036128 A1 | 2/2010 | Rezaie et al. | |
| 2010/0081817 A1 | 4/2010 | Hudson et al. | |
| 2013/0102780 A1 | 4/2013 | Giguere et al. | |

FOREIGN PATENT DOCUMENTS

| | | |
|---|---|---|
| GB | 939287 | 10/1963 |
| GB | 1260699 | 1/1972 |
| GB | 2000137 | 1/1979 |
| WO | WO 98/02033 A1 | 1/1998 |
| WO | WO 2004/072086 | 8/2004 |
| WO | WO 2008/132679 A1 | 11/2008 |
| WO | WO 2008/137672 A1 | 11/2008 |
| WO | WO 2009/044200 A1 | 4/2009 |

OTHER PUBLICATIONS

Beugelmans et al. (1994) *Tetrahedron Lett.* 35:4349-4350.
Bhatt et al. (1982) *Synthesis* 12:1048-1050.
Bois-Choussey et al. (1996) *J. Org. Chem.* 61:9309-9322.
Boss et al. (1976) *Angew. Chem., Int. Ed. Engl.* 15:558-559.
Bruce et al. (1981) *J. Chem. Res. Synop.* 7:193, 2564-2572.
Chiappe et al. (1998) *Asymmetry* 9:4079-4088.
Cooley et al. (Jan. 1989) *Synthesis*, pp. 1-7.
Coop et al. (1998) *J. Org. Chem.* 63:4392-4396.
Dang et al. (1990) *J. Org. Chem.* 55(6):1847-1851.
Denis et al. (2002) *Tetrahedron Lett.* 43:4171-4174.
Dessolin et al. (1995) *Tetrahedron Lett.* 36:5741-5744.
Dulayymi et al. (1996) *Tetrahedron* 52(10):3409-3424.
Fahrenholtz (1972) *J. Org. Chem.* 37(13):2204-2207.
Four et al. (1982) *Tetrahedron Lett.* 23:1825-1828.
Freund et al. (1917) *J. Prakt. Chem.* 94:135-178.
Fujino et al. (1967) *Chem. Pharm. Bull.* 15(12):2015-2016.
Garro-Helion et al. (1993) *J. Org. Chem.* 58:6109-6113.
Gerszberg et al. (1973) *Tetrahedron Lett.* 14(15):1269-1272.
Gesson et al. (Nov. 1990) *Synlett.*, pp. 669-670.
Greiner et al. (2004) *J. Med. Chem.* 46(9):1758-1763.
Guthikonda et al. (2002) *J. Am. Chem. Soc.* 124:13672-13673.
Hey et al. (1973) *Angew. Chem., Int. Ed. Engl.* 12:928-929.
Hosztafi et al. (1992) *Monatshefte für Chemie* 123:435-441.
Iijima et al. (1977) *Helvetica Chimica Acta* 60:2135-2137.
International Preliminary Report on Patentability dated Dec. 14, 2012 for International Application No. PCT/IB2011/001328.
International Search Report and Written Opinion dated Oct. 12, 2011 for International Application No. PCT/IB2011/001328.
Kametani et al. (1976) *J. Org. Chem.* 41:2545.
Kariyone et al. (1970) *Tetrahedron Lett.* 11(33):2885-2888.
Kim et al. (2006) *J. Am. Chem. Soc.* 128:16394-16397.
Kim et al. (2008) *Tetrahedron* 64:4209-4214.
Koreeda et al. (1984) *J. Org. Chem.* 49:2079-2082.
Krassnig et al. (1996) *Arch. Pharm. Med. Chem.* 329:325-326.
Krassnig et al. (1998) *Heterocycles* 47:1029-1032.
Mann et al. (1965) *J. Chem. Soc.* Paper 761, pp. 4120-4127.
Martin et al. (1982) *J Org. Chem.* 47:1513.
Martin et al. (1994) *J. Am. Chem. Soc.* 116:4493-4494.
McCamley et al. (2003) *J. Org. Chem. Soc.* 68:9847-9850.
Mellegaard-Waetzig et al. (2005, No. 18) *Synlett.*, pp. 2759-2762.
Menchaca et al. (2003) *J. Org. Chem.* 68:8859-8866.
Murahashi (1995) *Angew. Chem., Int. Ed. Engl.* 34:2443-2465.
Murahashi et al. (1988) *J. Am. Chem. Soc.* 110:8256-8258.
Murahashi et al. (1992) *Tetrahedron Lett.* 33:6991-6994.
Murahashi et al. (2003) *J. Am. Chem. Soc.* 125:15312-15313.
Ninan et al. (1992) *Tetrahedron* 48(32):6709-6716.
Notice of Reasons for Rejection for JP application No. 2013-513776 dated Mar. 25, 2014.
Novak et al. (2000) *Current Org. Chem.* 4:343-362.
Office Action and Search Report dated May 26, 2014 for Taiwan Invention Patent Application No. 100120389.
Office Action and Search Report dated May 26, 2014 for Taiwan Invention Patent Application No. 100120389—English translation.
Olah et al. (Sep. 1991) *Synthesis*, pp. 739-740.
Olofson et al. (1984) *J. Org. Chem.* 49(11):2081-2083.
Periasamy et al. (2000) *J. Org. Chem.* 65:3548-3550.
Polniaszek et al. (1992) *J. Org. Chem.* 57:4103-4110.
Rao (1982) *J. Org. Chem.* 47:369-371.
Rice et al. (1975) *J. Org. Chem.* 40(12):1850-1851.
Rosenau et al. (2004) *Org. Lett.* 6:541-544.
Saaby et al. (2000) *Angew. Chem., Int. Ed., Engl.* 39(22):4114-4116.
Sakuma et al. (2005) *Tetrahedron* 61:10138-10145.
Santamaria et al. (1989) *Tetrahedron Lett.* 30:2927-2928.
Santamaria et al. (1990) *Tetrahedron Lett.* 31:4735-4738.
Schmidhammer et al. (1989) *Helvetica Chimica Acta, Verlag Helvetical Chimica Acta* 72(6):1233-1240.
Schwartz et al. (1981) *J. Med. Chem.* 24:1525-1528.
Small (1938) *J. Org. Chem.* 3:204-232.
Stattely et al. (2009) *J. Am. Chem. Soc.* 131:943-953.
Takai et al. (2003) *J. Am. Chem. Soc.* 125:12990-12991.
Tamaru (1987) *Tetrahedron Lett.* 28(30):3497-3500.
Thomas et al. (1997) *Tetrahedron Lett.* 38:4721-4724.
Torque et al. (2005) *Tetrahedron* 61:4811-4817.
Villani et al. (1986) *Arzneim-Forsch./Drug. Res.* 36(9):1311-1314.
Xu et al. (2008) *Org. Lett.* 10(7):1497-1500.
Yeh et al. (2006) *Bioorg. Med. Chem. Lett.* 16:5408-5413.
Zhang et al. (2005) *Org. Lett.* 7:3239-3242.

\* cited by examiner

PROCESS FOR N-DEALKYLATION OF TERTIARY AMINES

1. FIELD

This application is a continuation of application Ser. No. 13/711,288, filed Dec. 11, 2012, now U.S. Pat. No. 8,921,556 B2, which is a continuation of International application serial no. PCT/IB2011/001328, filed Jun. 10, 2011, which claims the benefit under 35 U.S.C. §119(e) of provisional application No. 61/354,017, filed Jun. 11, 2010, the contents of all of which are incorporated herein by reference.

2. BACKGROUND

N-dealkylation of tertiary amines is a key chemical transformation in many processes for the preparation of clinically and commercially important compounds. Methods for N-dealkylation of tertiary amines are known in the art and include reaction of the tertiary amine with cyanogen bromide (see, e.g., U.S. Pat. No. 3,254,088; U.S. Pat. No. 3,433,791; and Cooley et al., "Amine Dealkylations with Acyl Chlorides" (1989) *Synthesis* 1-7), dialkyl azodicarboxylates including diethylazodicarboxylate and diisopropylazodicarboxylate, (see, e.g., GB 1,124,441), and haloformate reagents, including vinyl, methyl, ethyl, allyl, propyl, heptyl, phenyl, benzyl, α-chloro-ethyl, and 2,2,2-tri-chloro-ethyl chloroformates (see, e.g., U.S. Pat. Nos. 3,905,981 and 4,472,253; Olofson et al. (1984) *J. Org. Chem.* 49(11):2081-2083; and Rice et al. (1975) *J. Org. Chem.* 40(12):1850-1851).

Additional methods for N-dealkylation, particularly N-demethylation of tertiary amines, involve photochemical cleavage, as well as the formation and hydrolysis of dithiocarbamate, methyoxymethylether, and amine N-oxide intermediates to provide the corresponding secondary amine ("nor") derivatives (see, e.g., Santamaria et al. (1989) *Tetrahedron Lett.* 30:2927; Santamaria et al. (1990) *Tetrahedron Lett.* 31:4735; Acosta et al. (1994) *J. Chem. Soc., Chem. Commun.* 17(7):1985-1986; Murahashi et al. (1988) *J. Am. Chem. Soc.* 110:8256; Murahashi (1995) *Angew. Chem., Int. Ed., Engl.* 34:2443; Polniaszek et al. (1992) *J. Org. Chem.* 57:4103; Murahashi et al. (1992) *Tetrahedron Lett.* 33:6991; Murahashi et al. (2003) *J. Am. Chem. Soc.* 125:15312; McCamley et al. (2003) *J. Org. Chem. Soc.* 68:9847; Gesson et al., "Preparation of N-Demethyl and N-Alkyl Analogs of L-Rhodosamine" (November 1990) *Synlett.* 669-670; Rosenau et al. (2004) *Org. Lett.* 6:541; Menchaca et al. (2003) *J. Org. Chem.* 68:8859; Periasamy et al. (2000) *J. Org. Chem.* 65:3548; Saaby et al. (2000) *Angew. Chem., Int. Ed, Engl.* 39:4114-4116; Denis et al. (2002) *Tetrahedron Lett.* 43:4171; and Zhang et al. (2005) *Org. Lett.* 7:3239).

As set forth in these references, the tertiary amine is converted to an intermediate that is subsequently cleaved to provide the corresponding dealkylated (e.g., demethylated) secondary amine. The secondary amine can then be realkylated, e.g., by condensation with an alkyl or alkenyl halide selected from among propyl iodide, cyclopropyl methyl bromide, cyclobutyl methyl bromide, and allyl bromide (see, e.g., U.S. Pat. Nos. 3,905,981; 4,141,897; 3,254,088; 3,332,950; and 3,433,791). The secondary amine can also be alkylated using reductive amination, involving reaction of the secondary amine with an alkyl aldehyde to provide an imine intermediate that can be reduced to a tertiary alkyl amine by hydrogenation in the presence of a transition metal catalyst. Alternatively, the secondary amine can be alkylated with an acid chloride to provide an amide intermediate that can be reduced to the corresponding tertiary alkyl amine, e.g., with diisobutylaluminum hydride (DIBALH).

These reactions, however, can involve the use of materials and reagents that are relatively expensive, toxic and environmentally burdensome. Such processes can also require purification of intermediates, extended process times, and harsh reaction conditions, and can provide overall yields that are not commercially viable.

For example, methods for the preparation of semi-synthetic opiate derivatives, e.g., naloxone, naltrexone, nalorphine, nalmefene, and nalbuphine, all involve removal of the naturally occurring opioid N-methyl group followed by replacement of that group with another alkyl or an alkenyl moiety. The ultimate starting materials for preparation of these semi-synthetic compounds include the natural products morphine, codeine, thebaine, and oripavine. Among these, thebaine and oripavine are particularly useful because they are readily oxidized to introduce the 14-hydroxy group carried by each of the above semi-synthetic opiates. In a similar manner, the semi-synthetic processes for the synthesis of buprenorphine, levallorphan, pentazocine, cyclazocine, and ketazocine also involve replacement of an N-methyl group of a tertiary amine with an alkyl or an alkenyl moiety.

N-demethylation of opiates with chloroformate reagents has been carried out in chlorinated solvents like 1,2-dichloroethane (DCE), chloroform ($CHCl_3$) and dichloromethane ($CH_2Cl_2$). Where such solvents are employed in industrial scale commercial processes, the use of a halogenated solvent imposes additional process and environmental burdens, including, inter alia, the need for solvent exchanges where a protic solvent is required for hydrolysis of intermediates and products. In other instances, N-demethylation of opiates with chloroformate reagents has been carried out in acetonitrile. However, since acetonitrile is miscible in water, a solvent swap would be needed in order carry out aqueous washes of the reactions mixture after N-demethylation.

Accordingly, there remains a need for more efficient methods for the preparation of N-allyl derivatives of tertiary amines, as well as for improved processes incorporating those methods that would be robust, cost effective, amenable to commercial scale-up, and that would impose lower burdens on the environment. In particular, there remains a need for more efficient methods for the preparation of semi-synthetic opiate derivatives, including naloxone, naltrexone, nalmefene, nalbuphine, and buprenorphine, as well as levallorphan, pentazocine, cyclazocine, and ketazocine.

3. SUMMARY

As disclosed herein, N-dealkylation of a tertiary amine is mediated by reaction with a haloformate reagent carried out in solvents comprising a tertiary alcohol. The successful use of a tertiary alcohol as a solvent was a surprising and unexpected result in light of the expectation that protic solvents would react with the electrophilic reagents employed in N-dealkylation reactions. As demonstrated below, the use of solvents comprising a tertiary alcohol provides more efficient processes, particularly more efficient commercial processes, for dealkylation of tertiary amines including, for example, demethylation of opioid compounds and derivatives thereof. In certain embodiments, the N-dealkylation reactions disclosed herein are carried out in the presence of an iodide salt. In certain embodiments, the iodide salt is present in a substoichiometric amount. In certain embodiments, the iodide salt is present in a catalytic amount.

Exploitation of the dealkylation reactions disclosed herein provides more efficient processes for the preparation of clinically and commercially important semi-synthetic compounds from natural products and derivatives thereof. In particular illustrative embodiments, the methods and processes incorporating those methods that are disclosed herein are useful for the conversion of oxymorphone to noroxymorphone, for the conversion of oxymorphone to naloxone, for the conversion of oripavine to noroxymorphone, and for the conversion of oripavine to naloxone.

In one embodiment, the present disclosure provides a method for dealkylation of a tertiary amine in which the tertiary amine is contacted with a haloformate reagent in a solvent comprising a tertiary alcohol to provide the carbamate product. More specifically, the present disclosure is directed to a method for dealkylation of a tertiary amine of formula (1)

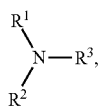

comprising contacting the compound of formula (1) with a compound of formula (2)

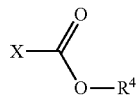

in a solvent to provide a compound of formula (3)

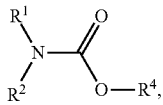

wherein the solvent comprises a tertiary alcohol. $R^1$, $R^2$, and $R^3$ are each independently selected from the group consisting of —$(C_1$-$C_6)$alkyl, —$(C_2$-$C_6)$alkenyl, —$(C_2$-$C_6)$alkynyl, aryl, and heteroaryl, each being unsubstituted or substituted with 1, 2, 3, 4, or 5 independently-selected $R^5$ groups. In certain embodiments, $R^1$ and $R^2$ are taken together with the nitrogen atom to which they are bound to form a heterocyclic or heteroaryl ring of formula (4)

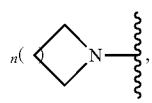

where n is an integer selected from the group consisting of 0, 1, 2, 3, 4, 5, 6, 7, 8, 9, 10, and 11. The heterocyclic or heteroaryl ring of formula (4) is a monocyclic ring that is saturated, unsaturated non-heteroaryl, or heteroaryl, which is unsubstituted or substituted with 1, 2, 3, 4, or 5 independently-selected $R^{20}$ groups, or is a subunit of a polycyclic ring system comprising any combination of 1, 2, 3, 4, 5, or 6 carbocyclic, heterocyclic, aryl, or heteroaryl rings, each of which is unsubstituted or substituted with 1, 2, 3, 4, or 5 independently-selected $R^{20}$ groups. Each $R^{20}$ is independently selected from the group consisting of =O, =$CH_2$, —$OR^{21}$, —$O(C_1$-$C_6)$alkyl, —$C(=O)(C_1$-$C_6)$alkyl, and —$(C_1$-$C_6)$alkyl, where each alkyl group is either unsubstituted or substituted with 1, 2, 3, 4, or 5 independently-selected —$OR^{21}$ groups. $R^{21}$ is —H or an oxygen protecting group. Accordingly, in certain embodiments, the compound of formula (1) is an opioid compound.

$R^4$ is selected from the group consisting of —$(C_1$-$C_6)$alkyl, —$(C_2$-$C_6)$alkenyl, —$(C_2$-$C_6)$alkynyl, aryl, and heteroaryl, each being unsubstituted or substituted with 1, 2, 3, 4, or 5 independently-selected $R^5$ groups, and each $R^5$ is independently selected from the group consisting of —OH, —Cl, —Br, —I, —$NH_2$, —CN, —O—$(C_1$-$C_6)$alkyl, and phenyl. X is selected from the group consisting of —Cl, —Br, —I, mesylate, and tosylate.

In certain embodiments, the present disclosure provides a method for dealkylation of a tertiary amine in which the tertiary amine is contacted with a haloformate reagent in a solvent comprising a tertiary alcohol to provide the carbamate product. More specifically, the present disclosure is directed to a method for dealkylation of a tertiary amine of formula (1)

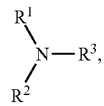

comprising contacting the compound of formula (1) with a compound of formula (2)

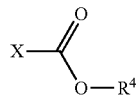

in a solvent to provide a compound of formula (3)

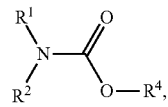

wherein the solvent comprises a tertiary alcohol. $R^1$, $R^2$, and $R^3$ are each independently selected from the group consisting of —$(C_1$-$C_6)$alkyl, —$(C_2$-$C_6)$alkenyl, —$(C_2$-$C_6)$alkynyl, aryl, and heteroaryl, each being unsubstituted or substituted with 1, 2, 3, 4, or 5 independently-selected $R^5$ groups. In certain embodiments, $R^1$ and $R^2$ are taken together with the nitrogen atom to which they are bound to form a heterocyclic or heteroaryl ring of formula (4)

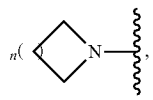

where n is an integer selected from the group consisting of 0, 1, 2, 3, 4, 5, 6, 7, 8, 9, 10, and 11. The heterocyclic or heteroaryl ring of formula (4) is a monocyclic ring that is saturated, unsaturated non-heteroaryl, or heteroaryl, which is unsubstituted or substituted with 1, 2, 3, 4, or 5 independently-selected $R^{20}$ groups, or is a subunit of a polycyclic ring system comprising any combination of 1, 2, 3, 4, 5, or 6 carbocyclic, heterocyclic, aryl, or heteroaryl rings, each of which is unsubstituted or substituted with 1, 2, 3, 4, or 5 independently-selected $R^{20}$ groups. Each $R^{20}$ is independently selected from the group consisting of =O, =CH$_2$, —OR$^{21}$, —O(C$_1$-C$_6$)alkyl, and —(C$_1$-C$_6$)alkyl, where each alkyl group is either unsubstituted or substituted with 1, 2, 3, 4, or 5 independently-selected —OR$^{21}$ groups. $R^{21}$ is —H or an oxygen protecting group. Accordingly, in certain embodiments, the compound of formula (1) is an opioid compound. $R^4$ is selected from the group consisting of —(C$_1$-C$_6$)alkyl, —(C$_2$-C$_6$)alkenyl, —(C$_2$-C$_6$)alkynyl, aryl, and heteroaryl, each being unsubstituted or substituted with 1, 2, 3, 4, or 5 independently-selected $R^5$ groups, and each $R^5$ is independently selected from the group consisting of —OH, —Cl, —Br, —I, —NH$_2$, —CN, and phenyl. X is selected from the group consisting of —Cl, —Br, —I, mesylate, and tosylate.

In certain embodiments, at least one of $R^1$, $R^2$, and $R^3$ of the tertiary amine of formula (1) is —(C$_1$-C$_6$)alkyl. In certain embodiments, $R^3$ is —(C$_1$-C$_6$)alkyl. In certain embodiments, at least one of $R^1$, $R^2$, and $R^3$ of the tertiary amine of formula (1) is methyl. In certain embodiments, $R^3$ is methyl.

In certain embodiments, the contacting of a compound of formula (1) with a compound of formula (2) is carried out in the presence of an iodide salt. In certain embodiments, the iodide salt is present in a sub-stoichiometric amount. In certain embodiments, the iodide salt is present in a catalytic amount.

In certain embodiments, compounds of formula (3) are hydrolyzed, typically with an acid or base, to provide the corresponding secondary amine ("nor" derivative), i.e., a compound of formula (22)

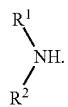

Compounds of formula (22) can be alkylated using methods and reagents known in the art. In certain, non-limiting examples, compounds of formula (22) are alkylated by contact with a compound of formula (10) X'—R$^{16}$ to provide compounds of formula (23)

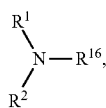

where X and X' are each independently selected from the group consisting of —Cl, —Br, —I, mesylate, and tosylate. $R^{16}$ can, in certain non-limiting examples, be selected from the group consisting of allyl, methylcyclopropyl, methylcyclobutyl, and propargyl.

In certain embodiments, alkylation of compounds of formula (22) with a compound of formula (10) is carried out in the presence of an iodide salt. In certain embodiments, the iodide salt is present in a sub-stoichiometric amount. In certain embodiments, the iodide salt is present in a catalytic amount.

In another embodiment, the present disclosure provides a method for demethylation of an opioid compound, in which the opioid is contacted with a haloformate reagent in a solvent comprising a tertiary alcohol to provide the carbamate product. More specifically, the present disclosure is directed to a method for making a compound of formula (7)

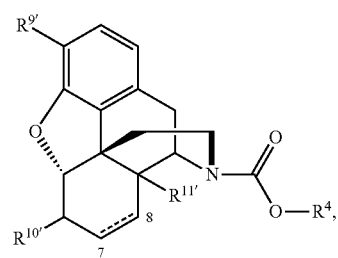

comprising contacting a compound of formula (6)

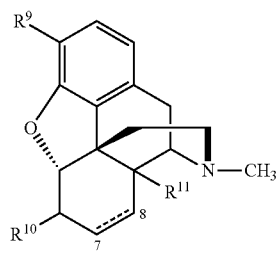

with a compound of formula (2)

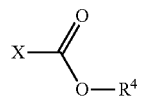

in a solvent to provide the compound of formula (7), where the ----- 7,8-bond is a single bond or a double bond, and the solvent comprises a tertiary alcohol. $R^9$ and $R^{11}$ are each independently selected from the group consisting of —OH, —H, and —OR$^{15}$, where $R^{15}$ is an oxygen protecting group. $R^{10}$ is selected from the group consisting of =O, =CH$_2$, —H, and —OR$^{15}$. $R^4$ is selected from the group consisting of —(C$_1$-C$_6$)alkyl, —(C$_2$-C$_6$)alkenyl, —(C$_2$-C$_6$)alkynyl, aryl, and heteroaryl, each being unsubstituted or substituted with 1, 2, 3, 4, or 5 independently-selected $R^5$ groups, and each $R^5$ is independently selected from the group consisting of —OH, —Cl, —Br, —I, —NH$_2$, —CN, —O—(C$_1$-C$_6$)alkyl, and phenyl. X is selected from the group consisting of —Cl, —Br, —I, mesylate, and tosylate.

As used throughout herein, it is to be understood that $R^{9'}$, $R^{10'}$, and $R^{11'}$ include not only $R^9$, $R^{10}$, and $R^{11}$, respectively, but also, when an $R^9$, $R^{10}$, and/or $R^{11}$ group is present as an —OH group or contains an —OH group, the reaction product of a compound of formula (2) with that —OH group to form a group comprising a carbonate (i.e., —OC(O)OR$^4$). Thus, $R^{9'}$, $R^{10'}$, and $R^{11'}$ groups include, in addition to the respective $R^9$, $R^{10}$, and $R^{11}$ groups, such carbonate-containing reaction products.

It is also to be understood that when $R^9$ is selected to be a particular moiety that is not an —OH group, then $R^{9'}$ is also that particular $R^9$ moiety. Likewise, it is to be understood that when $R^{10}$ is selected to be a particular moiety that is not an —OH group, then $R^{10'}$ is also that particular $R^{10}$ moiety. Likewise, it is to be understood that when $R^{11}$ is selected to be a particular moiety that is not an —OH group, then $R^{11'}$ is also that particular $R^{11}$ moiety.

In embodiments where an $R^{9'}$, $R^{10'}$, and/or $R^{11'}$ group(s) is or contains a carbonate-containing group formed from an —OH group, that carbonate-containing group can be converted back to the —OH group. Conversion of the carbonate-containing group to the —OH group can be carried out in the presence of a suitable base. In some embodiments, conversion of the carbonate group(s) at $R^{9'}$, $R^{10'}$, and/or $R^{11'}$ to the corresponding —OH group(s) is carried out in a separate step prior to cleavage of the carbamate to provide the corresponding secondary amine.

As noted above, the present disclosure provides a process through which a tertiary amine is converted to the corresponding secondary amine. In certain embodiments, the present disclosure provides a method for demethylation of an opioid compound in which the opioid is contacted with a haloformate reagent in a solvent, wherein that solvent comprises a tertiary alcohol, to provide a carbamate product, followed by cleavage of the carbamate to provide the corresponding secondary amine or "nor" derivative thereof. More specifically, the present disclosure is directed to a method for making a compound of formula (8)

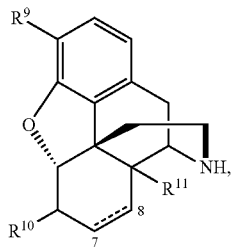

comprising contacting a compound of formula (6)

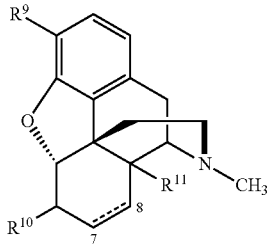

with a compound of formula (2)

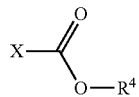

in a solvent to provide a compound of formula (7)

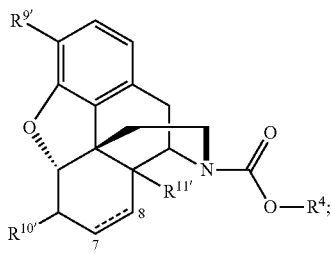

and converting the compound of formula (7) to the compound of formula (8), where the ------ 7,8-bond is a single bond or a double bond, and the solvent comprises a tertiary alcohol. $R^4$, $R^9$, $R^{9'}$, $R^{10}$, $R^{10'}$, $R^{11}$, $R^{11'}$, and X are as defined above.

In certain embodiments, the contacting of a compound of formula (6) with a compound of formula (2) is carried out in the presence of an iodide salt. In certain embodiments, the iodide salt is present in a sub-stoichiometric amount. In certain embodiments, the iodide salt is present in a catalytic amount.

In another embodiment, the present disclosure provides a process through which a tertiary amine is first dealkylated to the corresponding secondary amine which, in turn, is realkylated to a tertiary amine—providing a net replacement of one of the alkyl groups of the tertiary amine. One particular aspect of this embodiment therefore provides a process for replacement of the methyl group of an opioid, or a derivative thereof, with another moiety, which, in certain embodiments, is an unsubstituted or substituted alkyl moiety. In one embodiment, a tertiary amine is reacted with a haloformate ester in a solvent that comprises a tertiary alcohol, to provide a carbamate intermediate, and the carbamate intermediate is cleaved to provide the secondary amine product.

In certain embodiments, the tertiary amine is an opioid compound that is N-demethylated to the corresponding secondary amine, or "nor" derivative. More specifically, the present disclosure is directed to a method for making a compound of formula (9)

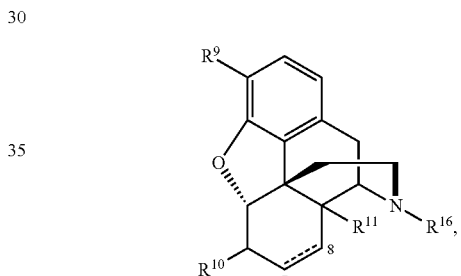

comprising:
(a) contacting a compound of formula (6)

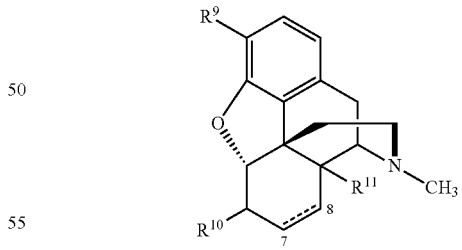

with a compound of formula (2)

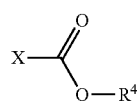

in a solvent to provide a compound of formula (7)

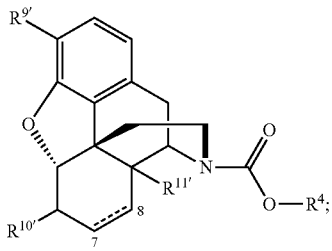

(b) converting the compound of formula (7) to a compound of formula (8)

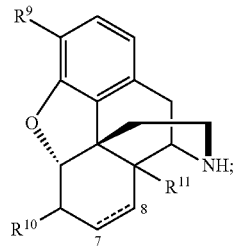

and (c) contacting the compound of formula (8) with a compound of formula (10) X'—R$^{16}$ to provide the compound of formula (9), where the ----- 7,8-bond is a single bond or a double bond, and the solvent comprises a tertiary alcohol. R$^4$, R$^9$, R$^{9'}$, R$^{10}$, R$^{10'}$, R$^{11}$, R$^{11'}$, R$^{16}$, and X are as defined above. X' is selected from the group consisting of —Cl, —Br, —I, mesylate, and tosylate.

In certain embodiments, the contacting of a compound of formula (6) with a compound of formula (2) is carried out in the presence of an iodide salt. In certain embodiments, the iodide salt is present in a sub-stoichiometric amount. In certain embodiments, the iodide salt is present in a catalytic amount.

In a further embodiment, the compound of formula (6) in each of the above embodiments is a compound of formula (19)

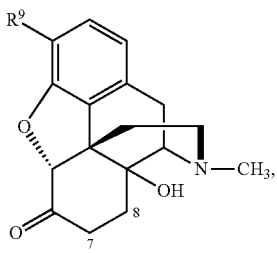

in which R$^9$ is selected from the group consisting of —OH, —H, and —OR$^{15}$, where R$^{15}$ is an oxygen protecting group. In certain embodiments, the compound of formula (19) is, in turn, prepared by oxidizing a compound of formula (20)

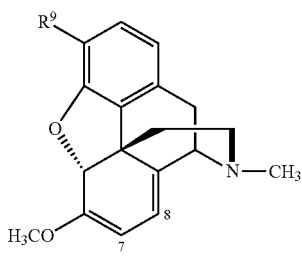

to provide a compound of formula (21)

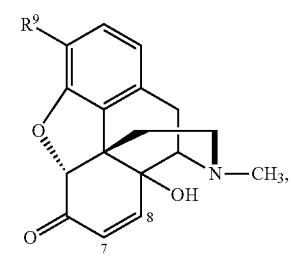

and hydrogenating the 7,8-double bond of the compound of formula (21) to provide the compound of formula (19). Again, R$^9$ is selected from the group consisting of —OH, —H, and —OR$^{15}$ where R$^{15}$ is an oxygen protecting group. In one embodiment, R$^9$ is —OH. In another embodiment, R$^9$ is —OCH$_3$.

In another embodiment, the present disclosure provides a method for making a compound of formula (11)

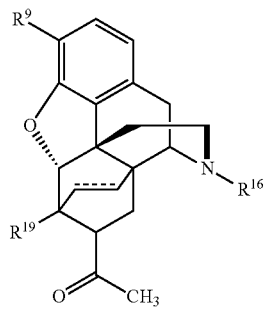

comprising (a) contacting a compound of formula (12)

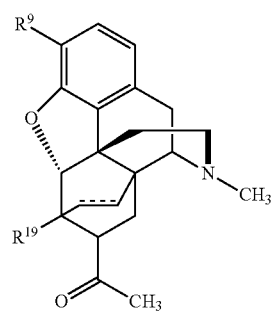

with a compound of formula (2)

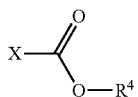

in a solvent to provide a compound of formula (13)

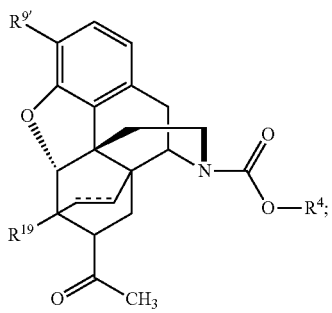

(b) converting the compound of formula (13) to a compound of formula (14)

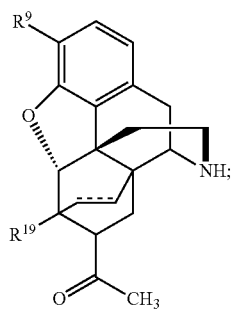

(c) contacting the compound of formula (14) with a compound of formula (10) $X'$—$R^{16}$ to provide the compound of formula (11), in which the ----- bond is a single bond or a double bond, and the solvent comprises a tertiary alcohol. $R^9$ and $R^{9'}$ are as defined above. $R^{19}$ is selected from the group consisting of —H, —CH$_3$, —OH, and —OR$^{15}$ where $R^{15}$ is an oxygen protecting group and $R^{16}$ is selected from the group consisting of allyl, methylcyclopropyl, methylcyclobutyl, and propargyl. $R^4$ is selected from the group consisting of —(C$_1$-C$_6$)alkyl, —(C$_2$-C$_6$)alkenyl, —(C$_2$-C$_6$)alkynyl, aryl, and heteroaryl, each being unsubstituted or substituted with 1, 2, 3, 4, or 5 independently-selected $R^5$ groups, and each $R^5$ is independently selected from the group consisting of —OH, —Cl, —Br, —I, —NH$_2$, —CN, —O—(C$_1$-C$_6$)alkyl, and phenyl. X and X' are each independently selected from the group consisting of —Cl, —Br, —I, mesylate, and tosylate.

In one embodiment, the contacting of step (a) is carried out in the presence of an iodide salt. In another embodiment, the contacting of step (c) is carried out in the presence of an iodide salt. In certain embodiments, the iodide salt is present in a sub-stoichiometric amount. In certain embodiments, the iodide salt is present in a catalytic amount.

In a further embodiment, the present disclosure provides a method for making a compound of formula (15)

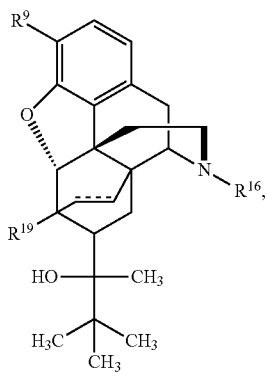

comprising
(a) contacting the compound of formula (16)

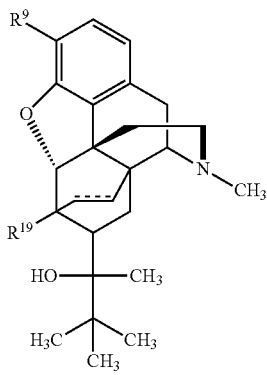

with a compound of formula (2)

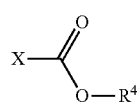

in a solvent to provide a compound of formula (17)

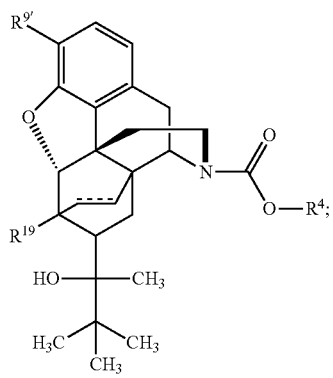

(b) converting the compound of formula (17) to a compound of formula (18)

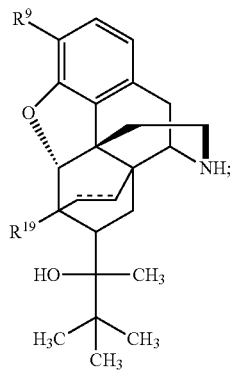

and (c) contacting the compound of formula (18) with a compound of formula (10) X'—R$^{16}$ to provide the compound of formula (15), in which the ------ bond is a single bond or a double bond, and the solvent comprises a tertiary alcohol. R$^4$, R$^9$, R$^{9'}$, R$^{16}$, R$^{19}$, X, and X' are as defined above.

In one embodiment, the contacting of step (a) is carried out in the presence of an iodide salt. In another embodiment, the contacting of step (c) is carried out in the presence of an iodide salt. In certain embodiments, the iodide salt is present in a sub-stoichiometric amount. In certain embodiments, the iodide salt is present in a catalytic amount.

The present disclosure is also directed to compositions prepared by combining a compound of formula (2), a tertiary alcohol, and a compound selected from the group consisting of a compound of formula (1), a compound of formula (6), a compound of formula (12), and a compound of formula (16). In certain embodiments, each composition can further comprise an iodide salt.

In other embodiments, the present disclosure also provides for a compound prepared by any method of the disclosure.

4. DETAILED DESCRIPTION

The present disclosure provides improved methods for the dealkylation of tertiary amines and, in particular, improved methods for N-demethylation of alkaloids—particularly opioids—in which a haloformate-mediated dealkylation reaction is carried out in a solvent comprising a tertiary alcohol. As demonstrated below, the use of a tertiary alcohol provides a number of advantages to the processes disclosed, including, but not limited to: (1) facilitating removal of water from reaction mixtures by azeotropic distillation, minimizing or eliminating side reactions, e.g., between water and haloformate reagents, (2) facilitating aqueous wash steps since the separated aqueous layer can be removed from the bottom of the vessel, and (3) facilitating solvent exchange into aqueous solvents typically used for hydrolysis of carbamate intermediates.

It has also been found that the dealkylation reactions and the realkylation reactions disclosed herein (see, e.g., Schemes 1, 3, 4, and 6), as well as processes comprising those reactions, can be improved by carrying those reactions out in the presence of an iodide salt, e.g., in the presence of a sub-stoichiometric amount or a catalytic amount of an iodide salt.

The present disclosure also provides improved processes for the preparation of clinically and commercially important semi-synthetic opioids.

In other embodiments, the present disclosure provides for a compound prepared by any method of the disclosure.

4.1 Definitions

As used herein, the following terms are intended to have the following meanings.

"—(C$_1$-C$_6$)alkyl" as used herein means a straight or branched hydrocarbon chain having 1, 2, 3, 4, 5, or 6 carbon atoms that can include or consist of a carbocyclic group. Representative straight chain —C$_1$-C$_6$ alkyls include methyl, -ethyl, -n-propyl, -n-butyl, -n-pentyl and -n-hexyl. Representative branched chain —C$_1$-C$_6$ alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, methylcyclopropyl, methylcyclobutyl, and the like.

"—(C$_2$-C$_6$)alkenyl" means a straight or branched hydrocarbon chain that can include a cyclic carbocyclic group, having 2, 3, 4, 5, or 6 carbon atoms and including at least one carbon-carbon double bond. Representative straight and branched chain (C$_2$-C$_6$)alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, 2-hexenyl, 3-hexenyl, and the like.

"—(C$_2$-C$_6$)alkynyl" means a straight or branched chain non-cyclic hydrocarbon having 2, 3, 4, 5, or 6 carbon atoms and including at least one carbon-carbon triple bond. Representative straight chain and branched (C$_2$-C$_6$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, and the like "Carbocyclic" as used herein refers to a ring structure in which all of the ring atoms are carbon. Representative carbocyclic groups include cyclopropyl, cyclobutyl, cyclopentyl and cyclohexyl.

"Heterocycle," as used herein encompasses, for example, -(3- to 7-membered)heterocycles, i.e., -(3- to 7-membered) heterocyclo rings, as defined below.

"-(3- to 7-membered)heterocycle" or "-(3- to 7-membered) heterocyclo" means a 3-, 4-, 5-, 6-, or 7-membered monocyclic ring having at least one heteroatom which is either saturated, unsaturated non-aromatic, or aromatic. A 3-membered heterocycle contains 1 heteroatom, a 4-membered heterocycle can contain 1 or 2 heteroatoms, a 5-membered heterocycle can contain 1, 2, 3, or 4 heteroatoms, a 6-membered heterocycle can contain 1, 2, 3, or 4 heteroatoms, and a 7-membered heterocycle can contain 1, 2, 3, 4, or 5 heteroatoms. Each heteroatom is independently selected from nitrogen, which can be quaternized; oxygen; and sulfur, including sulfoxide and sulfone. The -(3- to 7-membered)heterocycle can be attached via a nitrogen or carbon atom. Representative -(3- to 7-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

"Aryl" as used herein means a $C_6$-$C_{14}$ mono- or poly-cyclic aromatic ring system. Exemplary aryl groups include but are not limited to phenyl, naphthyl, anthryl, phenanthryl, and biphenyl groups.

"Heteroaryl" as used herein encompasses aromatic heterocycle rings that are -(5- to 10-membered)heteroaryl or -(5- or 6-membered)heteroaryl.

"-(5- to 10-membered)heteroaryl" means an aromatic heterocycle ring of 5, 6, 7, 8, 9, or 10 members, including both mono- and bicyclic ring systems, where at least one carbon atom of one or both of the rings is replaced with a heteroatom independently selected from nitrogen, oxygen, and sulfur, or at least two carbon atoms of one or both of the rings are replaced with a heteroatom independently selected from nitrogen, oxygen, and sulfur. In one embodiment, one of the -(5- to 10-membered)heteroaryl's rings contains at least one carbon atom. In another embodiment, both of the -(5- to 10-membered)heteroaryl's rings contain at least one carbon atom. Representative -(5- to 10-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, cinnolinyl, phthalazinyl, and quinazolinyl.

"-(5- or 6-membered)heteroaryl" means a monocyclic aromatic heterocycle ring of 5 or 6 members where at least one carbon atom is replaced with a heteroatom independently selected from nitrogen, oxygen, and sulfur. In one embodiment, one of the -(5- or 6-membered)heteroaryl's ring contains at least one carbon atom. Representative -(5- or 6-membered)heteroaryls include pyridyl, furyl, pyrrolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

"-Halogen" means —F, —Cl, —Br, or —I.

"Leaving group," means an atom or group that detaches from the rest of a molecule during a reaction, e.g., a group that is displaced in a substitution or elimination reaction.

"Oxygen protecting group," as used herein means a group introduced into a molecule by chemical modification that is capable of protecting an oxygen atom, particularly the oxygen atom of a free hydroxy group to obtain chemo selectivity in a subsequent chemical reaction and which, subsequent to the reaction for which protection is employed, can be removed without disturbing the remainder of the molecule. Representative, non-limiting examples of such oxygen protecting groups include acetyl, benzoyl, benzyl, β-methoxyethoxymethyl ether, dimethoxytrityl, methoxymethyl ether, p-methoxybenzyl, methylthiomethyl ether, pivaloyl, tetrahydropyranyl, trityl, silyl ether (trimethylsilyl, tert-butyldimethylsilyl, tert-butyldimethylsilyloxymethyl, and triisopropylsilyl, methyl ethers, and ethoxy ethers. In certain embodiments, an oxygen atom can be protected during a chemical reaction; e.g., the 3-hydroxy of an opioid compound can react with a haloformate reagent to provide a "protected" 3-carbonate derivative. As used herein, alkylated hydroxy groups are considered protected by the bound alkyl moiety; e.g., the 3-methoxy group of thebaine is considered, in this context, to carry a 3-hydroxy moiety protected by the bound methyl group. In a similar manner, hydroxy groups that react with a haloformate reagent to yielding a carbonate derivative are considered protected hydroxy groups; for example, reaction of a hydroxy group with allyl chloroformate provides a carbonate moiety as the product, (—OC(O)O—$CH_2$—CH=$CH_2$), represented as —$OR^{15}$, where the protecting group ("$R^{15}$") is the allyl oxycarbonyl moiety (—C(O)O—$CH_2$—CH=$CH_2$).

In connection with the heterocyclic or heteroaryl ring of formula (4) being a subunit of a polycyclic ring system comprising any combination of 1, 2, 3, 4, 5, or 6 carbocyclic, heterocyclic, aryl, or heteroaryl rings, each of which is unsubstituted or substituted with 1, 2, 3, 4, or 5 independently-selected $R^{20}$ groups, the following polycyclic ring systems are non-limiting examples of a heterocyclic ring of formula (4) being a subunit of a polycyclic ring system comprising a combination of 5 total carbocyclic, heterocyclic, and aryl rings, each of which is unsubstituted:

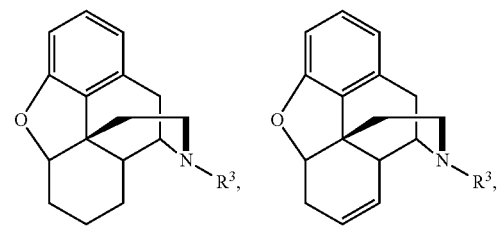

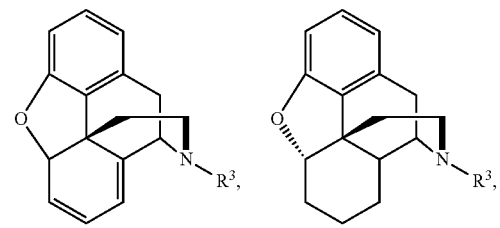

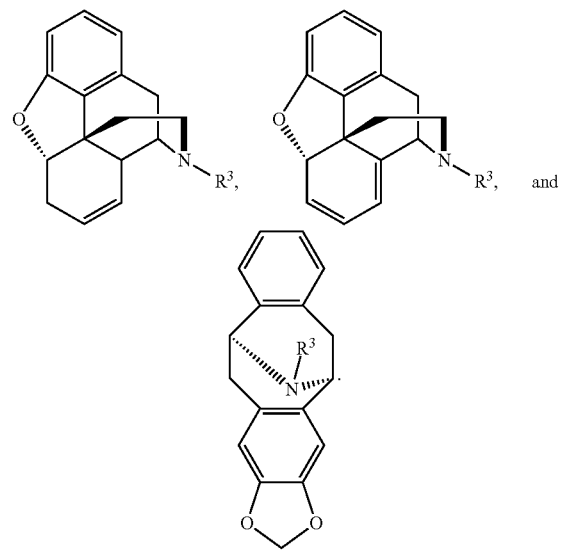

The following polycyclic ring systems are non-limiting examples of a heterocyclic ring of formula (4) being a subunit of a polycyclic ring system comprising a combination of 6 total carbocyclic, heterocyclic, and aryl rings, each of which is unsubstituted:

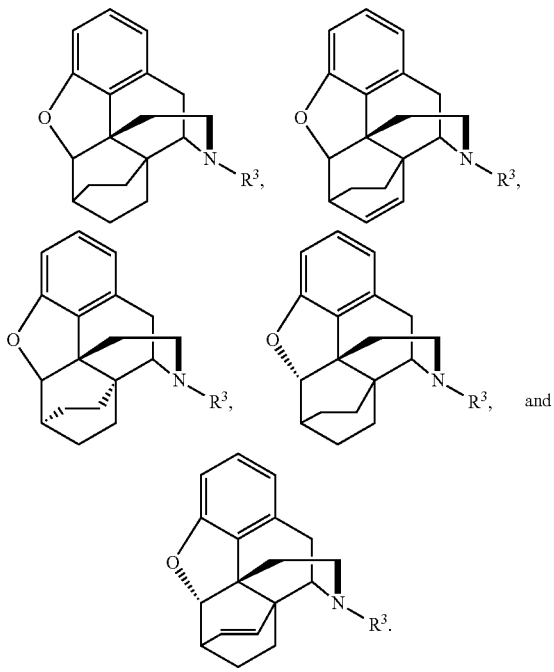

The following polycyclic ring systems are non-limiting examples of a heterocyclic ring of formula (4) being a subunit of a polycyclic ring system comprising a combination of 4 total rings, respectively, one each of a carbocyclic, heterocyclic, aryl, and heteroaryl ring, or one carbocyclic, 2 heterocyclic, and one aryl ring, each of which is unsubstituted:

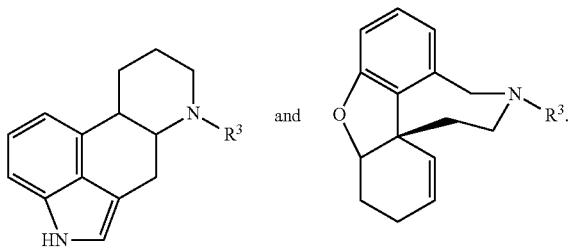

The following polycyclic ring systems are non-limiting examples of a heterocyclic ring of formula (4) being a subunit of a polycyclic ring system comprising a combination of 2 total rings, respectively, a combination of 2 heterocyclic rings or of one heterocyclic ring and one heteroaryl ring, each of which is unsubstituted:

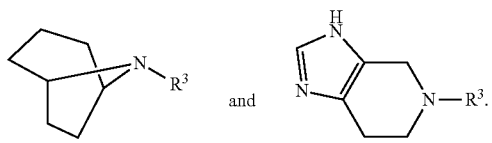

When a first group is "substituted with one or more" second groups, each of one or more of the first group's hydrogen atoms is replaced with an independently-selected second group. In one embodiment, a first group is substituted with one, two, or three independently-selected second groups. In another embodiment, a first group is substituted with one or two independently-selected second groups. In another embodiment, a first group is substituted with only one second group.

Numbering of the atoms in the structures disclosed herein is based upon the following scheme, using the chemical structure of morphine as the reference:

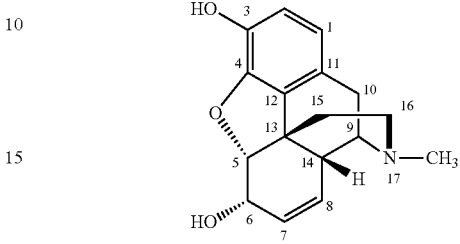

"CPS O" means a concentrate of poppy straw comprising oripavine as the main alkaloid. Such concentrates can be used directly in the reactions and processes disclosed herein that encompass the use of oripavine as a reagent.

"CPS T" means a concentrate of poppy straw comprising thebaine as the main alkaloid. Such concentrates can be used directly in the reactions and processes disclosed herein that encompass the use of thebaine as a reagent.

"Tertiary alcohol" as used herein refers to an alcohol of formula (5)

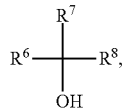

in which $R^6$, $R^7$, and $R^8$ are each independently —($C_1$-$C_6$) alkyl. Illustrative tertiary alcohols therefore include tert-amyl alcohol, tert-butyl alcohol, 3-methyl-3-pentanol, 2,3-dimethyl-3-pentanol, 3-ethyl-3-pentanol, and 2-methyl-2-hexanol, and mixtures of two or more thereof.

"Sub-stoichiometric amount" means an amount which is smaller than the stoichiometric amounts of a reactant(s) of the reactions described herein. For example, a sub-stoichiometric amount of the iodide salt used as catalyst in some embodiments is less than 100 mol % of the structure of formula (1). A sub-stoichiometric amount can be any numerical value within the range of from 0.01 to 99 mol % of the starting reactant (compound (I)) or the compounds taking place in the reaction schemes described herein. In certain embodiments, the sub-stoichiometric amount is in the range of from 20 to 70 mol %, 25 to 65 mol % or 30 to 60 mol % of the starting reactant, e.g., 30 mol % or 60 mol %.

"Catalytic amount" is a sub-stoichiometric amount which is sufficient to exert a catalytic effect on the reactions described herein. Typically, a catalytic amount can be any numerical value within the range of from 0.01 to 99 mol % of the starting reactant (like compound (I)) or the compounds taking its place in the reaction schemes described herein. In certain embodiments, the catalytic amount is in the range of from 20 to 70 mol %, 25 to 65 mol % or 30 to 60 mol % of the starting reactant or can be any numerical value within these ranges, e.g., 30 mol % or 60 mol %. In certain other embodiments, the catalytic amount is in the range of from 0.001 to 60 mol %, 0.01 to 40 mol %, 0.1 to 20 mol %, or 0.1 to 10 mol % of the starting reagent.

"Consisting essentially of" in certain embodiments of present disclosure means that the subsequently named component(s) is necessarily included but that another unlisted ingredient(s) that does not materially affect the basic and novel properties can also be present. In certain embodiments, the subsequently named component is the major component of the compound named before the term, e.g., a solvent consisting essentially of a tertiary alcohol (i.e., a compound of formula (5)) contains said tertiary alcohol (or said mixture of tertiary alcohols, see above) as major component, typically in an amount of more than 50 vol %, and other solvents (e.g., 1,2-dichloroethane, chloroform, dichloromethane, or acetonitrile) in a total amount of less than 50 vol %. In these embodiments, "consisting essentially of" means "comprising between 50 vol % and 100 vol % or any numeric value within this range of the subsequently named compound." In certain embodiments, "consisting essentially of" means "comprising from 80 to up to 100 vol % (excepting 100 vol %, as this is represented by "consisting of" in the context of present disclosure) or any numeric value within this range of the subsequently named compound, e.g., as in "a solvent comprising from 80 to up to 100 vol % tertiary alcohol".

In the event of doubt as to the agreement of a depicted chemical structure and a chemical name, the depicted chemical structure governs.

It will be appreciated that various features of the disclosure which are, for clarity, described in the context of separate embodiments, can also be provided in combination in a single embodiment unless otherwise specifically herein excluded. Conversely, various features of the disclosure which are, for brevity, described in the context of a single embodiment, can also be provided separately and/or in any suitable subcombination unless otherwise specifically herein excluded.

4.2 N-Dealkylation of Tertiary Amines

4.2.1 N-Dealkylation of Tertiary Amines—Carbamate Formation

In one embodiment, the present disclosure provides a process for the dealkylation of tertiary amines that comprises contacting the tertiary amine with a haloformate reagent in the presence of a tertiary alcohol to provide the corresponding dealkylated carbamate, as depicted in Scheme 1.

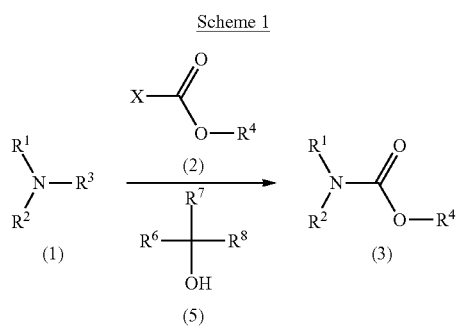

Among the three R groups ($R^1$, $R^2$, and $R^3$) attached to the nitrogen atom of the tertiary amine of formula (1), the group removed in the dealkylation reaction can be predicted according to the following hierarchy: benzyl>allyl>cycloxhexyl>methyl (see, e.g., Cooley et al., "Amine Dealkylations with Acyl Chlorides" (1989) *Synthesis* 1-7). In certain embodiments, e.g., those in which each of $R^1$, $R^2$, and $R^3$ is an alkyl group, it may be predicted that the least sterically hindered moiety will be the group displaced in the dealkylation reaction. In addition, where $R^1$ and $R^2$ are taken together with the nitrogen atom to which they are bound to form a heterocyclic or heteroaryl ring of formula (4), where n is as defined above, then it is predicted that $R^3$ would be the chemical group removed in the dealkylation reaction.

Compounds disclosed herein can contain one or more asymmetric centers and can thus give rise to enantiomers, diastereomers, and other stereoisomeric forms. In reference to compounds of formula (1) for example, as well as all other compounds described herein that contain one or more olefinic double bonds or other centers of geometric asymmetry, unless specified otherwise, they are intended to include both E and Z geometric isomers. The methods disclosed herein can be used with each of the enantiomers, diastereomers, and other stereoisomeric forms of the reagents disclosed herein to provide each of the enantiomers, diastereomers, and other stereoisomeric forms of the products disclosed herein.

The present disclosure provides a method for dealkylation of a tertiary amine of formula (1)

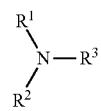

comprising contacting the compound of formula (1) with compound of formula (2)

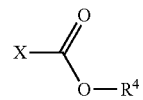

in a solvent to provide a compound of formula (3)

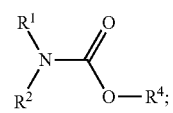

wherein the solvent comprises a tertiary alcohol.

$R^1$, $R^2$, and $R^3$ are each independently selected from the group consisting of —($C_1$-$C_6$)alkyl, —($C_2$-$C_6$)alkenyl, —($C_2$-$C_6$)alkynyl, aryl, and heteroaryl, each being unsubstituted or substituted with 1, 2, 3, 4, or 5 independently-selected $R^5$ groups, or $R^1$ and $R^2$ are taken together with the nitrogen atom to which they are bound to form a heterocyclic or heteroaryl ring of formula (4)

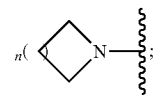

n is an integer selected from the group consisting of 0, 1, 2, 3, 4, 5, 6, 7, 8, 9, 10, and 11. The heterocyclic or heteroaryl ring of formula (4) is a monocyclic ring that is saturated, unsaturated non-heteroaryl, or heteroaryl, which is unsubstituted or substituted with 1, 2, 3, 4, or 5 independently-selected $R^{20}$ groups, or is a subunit of a polycyclic ring system comprising any combination of 1, 2, 3, 4, 5, or 6 carbocyclic, heterocyclic, aryl, or heteroaryl rings, each of which is unsubstituted or substituted with 1, 2, 3, 4, or 5 independently-selected $R^{20}$ groups. Each $R^{20}$ is independently selected from the group consisting of =O, =CH$_2$, —OR$^{21}$, —O(C$_1$-C$_6$)alkyl, —C(=O)(C$_1$-C$_6$)alkyl, and —(C$_1$-C$_6$)alkyl, where each alkyl group is either unsubstituted or substituted with 1, 2, 3, 4, or 5 independently-selected —OR$^{21}$ groups. $R^{21}$ is —H or an oxygen protecting group. Accordingly, in certain embodiments, the compound of formula (1) is an opioid compound.

$R^4$ is selected from the group consisting of —(C$_1$-C$_6$)alkyl, —(C$_2$-C$_6$)alkenyl, —(C$_2$-C$_6$)alkynyl, aryl, and heteroaryl, each being unsubstituted or substituted with 1, 2, 3, 4, or 5 independently-selected $R^5$ groups, where each $R^5$ is independently selected from the group consisting of —OH, —Cl, —Br, —I, —NH$_2$, —CN, —O—(C$_1$-C$_6$)alkyl, and phenyl. X is selected from the group consisting of —Cl, —Br, —I, mesylate, and tosylate. In certain embodiments of this method, the solvent is a tertiary alcohol or consists essentially of a tertiary alcohol. In other embodiments, the solvent comprises a tertiary alcohol.

The tertiary alcohol is an alcohol of formula (5)

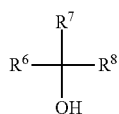

(5)

wherein $R^6$, $R^7$, and $R^8$ are each independently —(C$_1$-C$_6$) alkyl. Therefore, for example, the tertiary alcohol can be selected from the group consisting of tert-amyl alcohol, tert-butyl alcohol, 3-methyl-3-pentanol, 2,3-dimethyl-3-pentanol, 3-ethyl-3-pentanol, 2-methyl-2-hexanol, and mixtures of two or more thereof. In particular embodiments, the tertiary alcohol is tert-amyl alcohol.

In certain embodiments of the dealkylation reaction, contacting the compound of formula (1) with the compound of formula (2) is carried out in the presence of an iodide salt. In certain embodiments, the iodide salt is present in a substoichiometric amount. In certain embodiments, the iodide salt is present in a catalytic amount. The iodide salt can be selected from the group consisting of NaI, KI, LiI, CsI, RuI, MgI$_2$, CaI$_2$, NH$_4$I, tetrabutylammonium iodide, and combinations of two or more thereof. In particular embodiments, the iodide salt is NaI.

In certain embodiments, $R^3$ is —CH$_3$ and the method of Scheme 1 is a demethylation reaction. In another embodiment, $R^4$ is —(C$_1$-C$_6$)alkyl, each alkyl being either unsubstituted or substituted with 1, 2, 3, 4, or 5 independently-selected $R^5$ groups.

In other embodiments, the compound of formula (2) is selected from the group consisting of α-chloroethylchloroformate, trichloroethylchloroformate, allylchloroformate, methylchloroformate, ethylchloroformate, propylchloroformate, isopropylchloroformate, butylchloroformate, isobutylchloroformate, tert-butylchloroformate, phenylchloroformate, benzylchloroformate, methoxymethylchloroformate, vinylchloroformate, 2-chloroethylchloroformate, and any mixture thereof. In a particular embodiment, $R^4$ is ethyl and X is chloro, i.e., the compound of formula (2) is ethylchloroformate.

4.2.2 N-Dealkylation of Tertiary Amines—"Nor" Derivative Formation

In another embodiment, the present disclosure provides a process for the conversion of a tertiary amine to a secondary amine. This process comprises, as a first step, the reaction depicted in step (S1) of Scheme 2 below, whereby the tertiary amine is converted to a carbamate derivative in a solvent comprising a tertiary alcohol, followed by step (S2) in which the carbamate is converted to the secondary amine of formula (22).

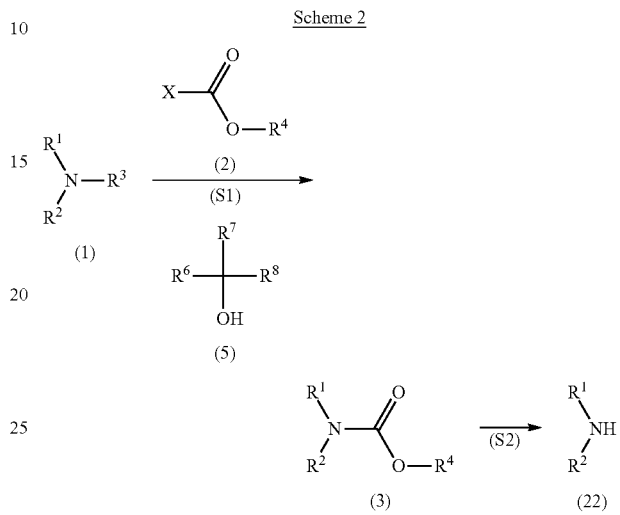

Cleavage of the carbamate moiety to provide compounds of formula (22) can be achieved by contact with aqueous mineral acid, e.g., sulfuric acid or hydrochloric acid in water.

4.2.3 Preparation of N-Alkyl Derivatives—Alkyl Substitution

In a further embodiment, the present disclosure provides a three-step process through which an alkyl moiety of a tertiary amine is replaced with a different moiety, such as, for example, an alkyl, alkenyl, alkynyl, aryl alkyl, or heteroaryl moiety. The first two steps in this process are those depicted in Schemes 3 below, whereby the tertiary amine is converted in step (S1) to a carbamate derivative, followed by step (S2) in which that carbamate is converted to the secondary amine. In step (S3), the secondary amine is reacted with a suitable reagent, e.g., an alkylating agent of formula (10), to provide a compound of formula (23).

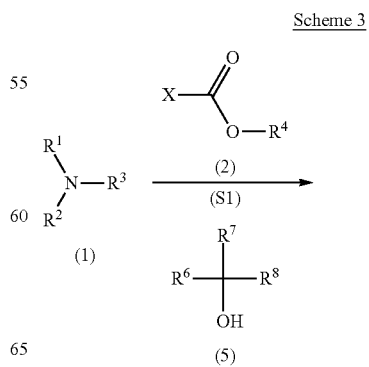

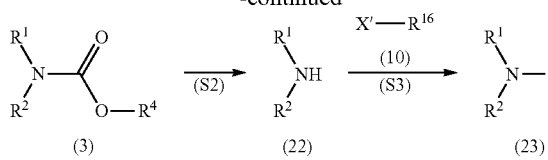

Conversion of compound of formula (22) to compounds of formula (23) can be accomplished using reagents and methods know in the art in view of this disclosure. In one embodiment, the compound of formula (22) is contacted with a compound of formula (10), in which X' is selected from the group consisting of —Br, —Cl, and —I. In a particular embodiment, X is —Br. In certain embodiments, moiety $R^{16}$ of compounds of formula (10) is selected from the group consisting of allyl, methylcyclopropyl, methylcyclobutyl, and propargyl. In a particular embodiment, $R^{16}$ is an allyl moiety.

In certain embodiments, either or both of step (S1) and step (S3) of Scheme 3 can be carried out in the presence of an iodide salt. In certain embodiments, the iodide salt is present in a sub-stoichiometric amount. In certain embodiments, the iodide salt is present in a catalytic amount. The iodide salt can be selected from the group consisting of NaI, KI, LiI, CsI, RuI, $MgI_2$, $CaI_2$, $NH_4I$, tetrabutylammonium iodide, and combinations of two or more thereof. In particular embodiments, the iodide salt is NaI.

4.3 N-Dealkylation of Opioids—Carbamate Formation

As noted above, the present disclosure provides processes for haloformate mediated N-dealkylation of tertiary amines of formula (1) in a solvent comprising, consisting essentially of, or consisting of a tertiary alcohol. The processes disclosed herein are also useful for dealkylating compounds (tertiary amines) comprising the structural elements of compounds of formula (1), including but, not limited to, alkaloids, and more particularly, opioid compounds and derivatives thereof carrying an N-methyl group.

For example, the present disclosure provides a process for the conversion of a tertiary amine to a secondary amine. This process comprises, as a first step, the reaction depicted in Scheme 1 above, whereby the tertiary amine is converted to a carbamate derivative, followed by a second step in which the carbamate is converted to the secondary amine, as depicted in Scheme 2. Accordingly, in another embodiment, the present disclosure provides a process for the demethylation of opioids and opioid derivatives that comprises contacting the opioid or opioid derivative with, for example, a haloformate reagent, in the presence of a tertiary alcohol, to provide the corresponding demethylated carbamate as depicted in Scheme 4.

Scheme 4

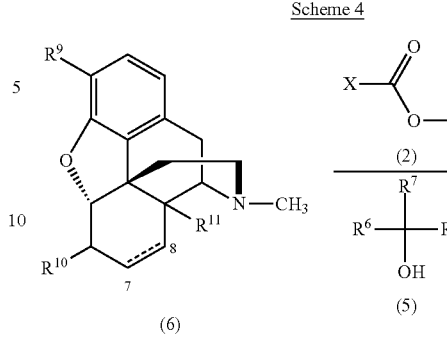

In certain embodiments, the tertiary amine is an opioid compound, and the present disclosure therefore provides a method for N-demethylating a compound of formula (6)

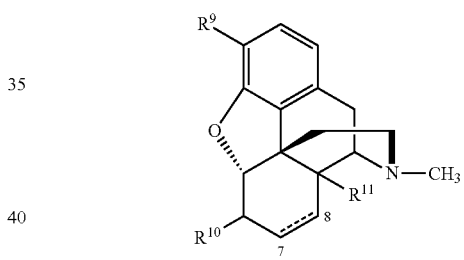

comprising contacting the compound of formula (6) with a compound of formula (2)

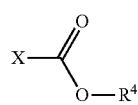

in a solvent to provide a compound of formula (7)

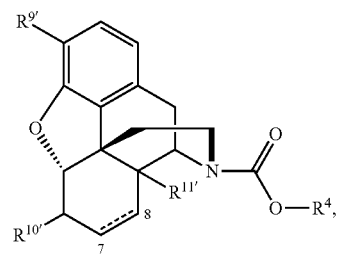

in which the ----- 7,8-bond is a single bond or a double bond, and the solvent comprises a tertiary alcohol. $R^4$, $R^9$, $R^{9'}$, $R^{10}$, $R^{10'}$, $R^{11}$, $R^{11'}$, and X are as defined above.

In certain embodiments, the solvent comprises, consists essentially of, or consists of a tertiary alcohol. The tertiary alcohol is an alcohol of formula (5)

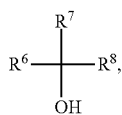

in which $R^6$, $R^7$, and $R^8$ are each independently —($C_1$-$C_6$) alkyl. The tertiary alcohol therefore can be selected from the group consisting of tert-amyl alcohol, tert-butyl alcohol, 3-methyl-3-pentanol, 2,3-dimethyl-3-pentanol, 3-ethyl-3-pentanol, 2-methyl-2-hexanol, and mixtures of two or more thereof. In certain embodiments, the tertiary alcohol is tert-amyl alcohol.

In certain embodiments, the ----- 7,8-bond of the compound of formula (6) is a single bond. In a particular embodiment, $R^9$ and $R^{11}$ are —OH and $R^{10}$ is =O. In another embodiment, $R^9$ is —$OCH_3$, $R^{11}$ is —OH, and $R^{10}$ is =O.

In other specific embodiments, the haloformate reagent is a compound of formula (2)

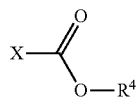

which can be selected from the group consisting of α-chloroethylchloroformate, trichloroethylchloroformate, allylchloroformate, methylchloroformate, ethylchloroformate, propylchloroformate, isopropylchloroformate, butylchloroformate, isobutylchloroformate, tert-butylchloroformate, phenylchloroformate, benzylchloroformate, methoxymethylchloroformate, vinylchloroformate, 2-chloroethylchloroformate, and any mixture thereof. In certain embodiments, $R^4$ is —($C_1$-$C_6$)alkyl, with the alkyl moiety being either unsubstituted or substituted with 1, 2, 3, 4, or 5 independently-selected $R^5$ groups while, in a specific embodiment, $R^4$ is ethyl. In a particular embodiment, $R^4$ is ethyl and X is —Cl, i.e., the haloformate compound of formula (2) is ethyl chloroformate (compound (42)).

In certain embodiments, each oxygen protecting group, $R^{15}$, is independently selected from the group consisting of tert-butyl-diphenylsilyl, tert-butyl-dimethylsilyl, trimethylsilyl, tri-iso-propylsilyl, tert-butyldimethylsilyloxymethyl, β-methoxyethoxymethyl, [bis-(4-methoxyphenyl)phenylmethyl)], methoxymethyl, p-methoxybenzyl, methylthiomethyl, pivaloyl, ethoxyethyl, triphenylmethyl, —C(O)$R^{17}$, —C(O)$OR^{18}$, —($C_1$-$C_6$)alkyl, —($C_2$-$C_6$)alkenyl, —($C_2$-$C_6$)alkynyl, aryl, and heteroaryl, each alkyl, alkynyl alkenyl, aryl, and heteroaryl being unsubstituted or substituted with 1, 2, 3, 4, or 5 independently-selected $R^5$ groups. Each $R^{17}$ and each $R^{18}$ is each independently selected from the group consisting of —($C_1$-$C_6$)alkyl, —($C_2$-$C_6$)alkenyl, —($C_2$-$C_6$)alkynyl, aryl, and heteroaryl, each being unsubstituted or substituted with 1, 2, 3, 4, or 5 independently-selected $R^5$ groups. Each $R^5$ is independently selected from the group consisting of —OH, —Cl, —Br, —I, —$NH_2$, —CN, —O—($C_1$-$C_6$)alkyl, and phenyl.

In particular embodiments, each oxygen protecting group, $R^{15}$, is independently selected from the group consisting of methyl, ethyl, iso-butyl, acetyl, benzyl, benzoyl, allyl, allyloxycarbonyl, phenyl, phenyloxycarbonyl, and —($C_1$-$C_6$) alkyloxycarbonyl.

In particular embodiments, $R^{9'}$ is —$OR^{15}$ and $R^{15}$ is —C(O) $OR^{18}$ and, in certain embodiments, $R^{18}$ is iso-butyl while, in other embodiments, $R^{18}$ is ethyl.

In certain embodiments, the dealkylation reaction depicted in Scheme 4 is carried out in the presence of an iodide salt. In certain embodiments, the iodide salt is present in a sub-stoichiometric amount. In certain embodiments, the iodide salt is present in a catalytic amount. The iodide salt can be selected from the group consisting of NaI, KI, LiI, CsI, RuI, $MgI_2$, $CaI_2$, $NH_4I$, tetrabutylammonium iodide, and combinations of two or more thereof. In one embodiment, the iodide salt is NaI.

4.4 N-Dealkylation of Opioids—Preparation of N-Demethylated "Nor" Derivatives In another embodiment, the disclosure provides processes for demethylation of an N-methyl opioid derivative to the corresponding N-nor derivative. These processes comprise step (S1), depicted in Scheme 5 below, whereby the opioid derivative is converted to a carbamate derivative, followed by step (S2) in which the carbamate is converted to the corresponding N-nor derivative.

Scheme 5

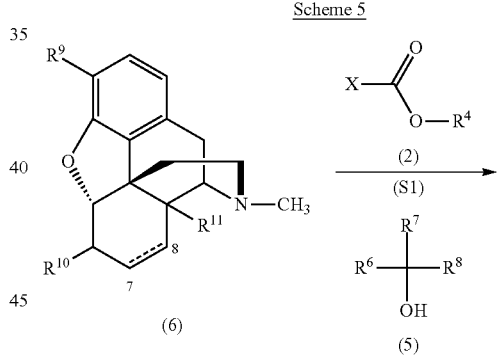

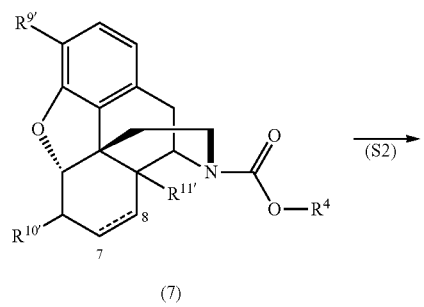

-continued

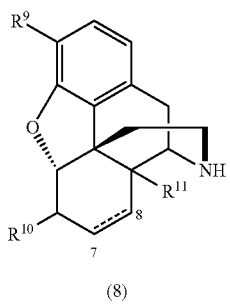

(8)

In certain embodiments therefore the present disclosure provides a method for making a compound of formula (8)

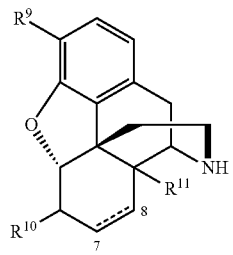

comprising contacting a compound of formula (6)

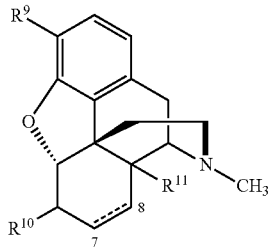

with a compound of formula (2)

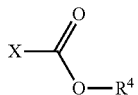

in a solvent to provide a compound of formula (7)

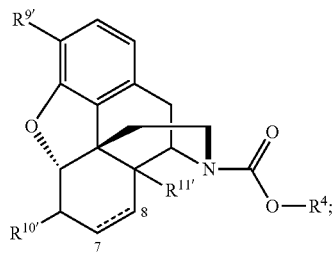

and converting the compound of formula (7) to the compound of formula (8), in which the ----- 7,8-bond is a single bond or a double bond, and the solvent comprises a tertiary alcohol. $R^4$, $R^6$, $R^7$, $R^8$, $R^9$, $R^{9'}$, $R^{10}$, $R^{10'}$, $R^{11}$, $R^{11'}$, and X are as defined above.

In certain embodiments, the solvent comprises, consists essentially of, or consists of a tertiary alcohol as defined above.

In certain embodiments, the ----- 7,8-bond of the compounds of formulae (6), (7), and (8) is a single bond. In certain embodiments, $R^9$ and $R^{11}$ are —OH and $R^{10}$ is =O while, in other embodiments, $R^9$ is —OCH$_3$, $R^{11}$ is —OH, and $R^{10}$ is =O.

In other specific embodiments the haloformate reagent is a compound of formula (2),

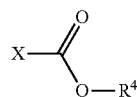

as defined above.

Each oxygen protecting group, $R^{15}$, can be independently selected from the group defined above.

In one embodiment, the contacting of the compound of formula (8) with the compound of formula (2) is carried out in the presence of an iodide salt. In certain embodiments, the iodide salt is present in a sub-stoichiometric amount. In certain embodiments, the iodide salt is present in a catalytic amount. In certain embodiments, the iodide salt is selected from the group defined above.

In certain embodiments, converting the compound of formula (7) to a compound of formula (8) is carried out in the presence of an acid. In certain embodiments, the acid is a mineral acid. In one embodiment, the acid is sulfuric acid. In another embodiment, the acid is hydrochloric acid.

4.5 Alkyl Substitution of the Opioid N-Methyl Group

In one embodiment, the present disclosure provides a method for the net replacement of an N-methyl group of an opioid with an unsubstituted or substituted alkyl, alkenyl, or alkynyl substituent. In certain embodiments therefore the disclosure provides a process for demethylation of an N-methyl opioid compound of formula (6) to the corresponding N-nor derivative, i.e., a compound of formula (8), and realkylation of the N-nor derivative with a compound of formula (10) to provide a compound of formula (9), as depicted in Scheme 6.

Scheme 6

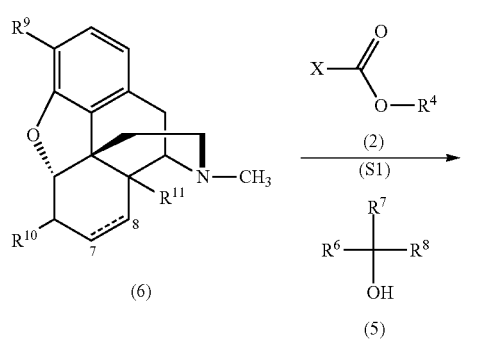

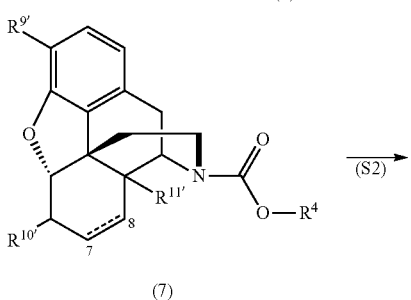

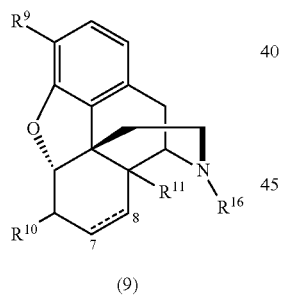

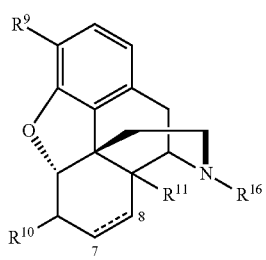

Accordingly, the present disclosure provides a method for making a compound of formula (9)

comprising (a) contacting a compound of formula (6)

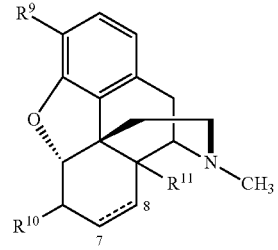

with a compound of formula (2)

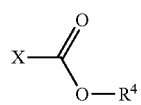

in a solvent to provide a compound of formula (7)

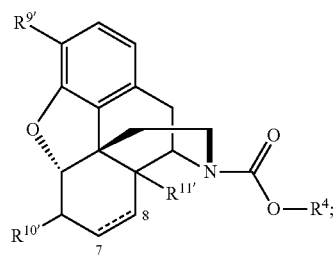

(b) converting the compound of formula (7) to a compound of formula (8)

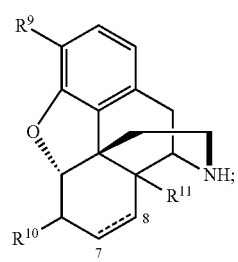

and (c) contacting the compound of formula (8) with a compound of formula (10) $X'$—$R^{16}$ to provide the compound of formula (9), in which the ----- 7,8-bond is a single bond or a double bond, and the solvent comprises a tertiary alcohol. $R^4$, $R^6$, $R^7$, $R^8$, $R^9$, $R^{9'}$, $R^{10}$, $R^{10'}$, $R^{11}$, $R^{11'}$, $R^{16}$, X, and X' are as defined above.

In certain embodiments, the solvent comprises, consists essentially of, or consists of a tertiary alcohol. The tertiary alcohol is a compound of formula (5)

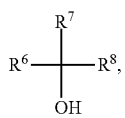

in which $R^6$, $R^7$, and $R^8$ are each independently —$(C_1-C_6)$ alkyl. The tertiary alcohol therefore can be selected from the group consisting of tert-amyl alcohol, tert-butyl alcohol, 3-methyl-3-pentanol, 2,3-dimethyl-3-pentanol, 3-ethyl-3-pentanol, 2-methyl-2-hexanol, and mixtures of two or more thereof. In a particular embodiment, the tertiary alcohol is tert-amyl alcohol.

In certain embodiment, the ----- 7,8-bond of the compounds of formulae (6), (7), (8), and (9) is a single bond. In one embodiment, $R^9$ and $R^{11}$ are —OH and $R^{10}$ is =O. In another embodiment, $R^9$ is —OCH$_3$, $R^{10}$ is =O, and $R^{11}$ is —OH.

In other specific embodiments the haloformate reagent is a compound of formula (2),

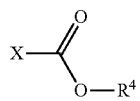

as defined above.

Each oxygen protecting group, $R^{15}$, is independently selected from the group defined above.

In another embodiment, step (a) is carried out in the presence of an iodide salt and in a further embodiment, step (c) is carried out in the presence of an iodide salt. In certain embodiments, the iodide salt is present in a sub-stoichiometric amount. In certain embodiments, the iodide salt is present in a catalytic amount. The iodide salt can be selected from the group as defined above.

In a particular embodiment, $R^{16}$ is allyl, $R^9$ is —OH, $R^{10}$ is =O, $R^{11}$ is —OH, and the ----- 7,8-bond is a single bond.

In certain embodiments, conversion of the compound of formula (7) to a compound of formula (8), comprises contacting the compound of formula (7) with a base to provide the compound of formula (8). In certain embodiments, the base is selected from the group consisting of Na$_2$CO$_3$, K$_2$CO$_3$, Cs$_2$CO$_3$, Na$_3$PO$_4$, Na$_2$HPO$_4$, and combinations of two or more thereof. In a particular embodiment, the base is Na$_2$CO$_3$.

In other embodiments of the disclosed process, the starting material, i.e., a compound of formula (6), is derived from a natural product.

4.6 Process for the Preparation of Compounds of Formulae (7), (8), and (9) from Natural Products Schemes 4, 5, and 6 depict methods for conversion of compounds of formula (6) to compounds of formulae (7), (8), and (9), respectively. In certain embodiments, the compound of formula (6) is a compound of formula (19)

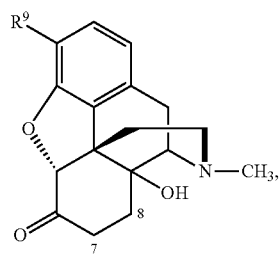

wherein $R^9$ is selected from the group consisting of —OH, —H, and —OR$^{15}$, where $R^{15}$ is an oxygen protecting group. Compounds of formula (19) can be prepared according to the methods depicted in Scheme 7.

Scheme 7

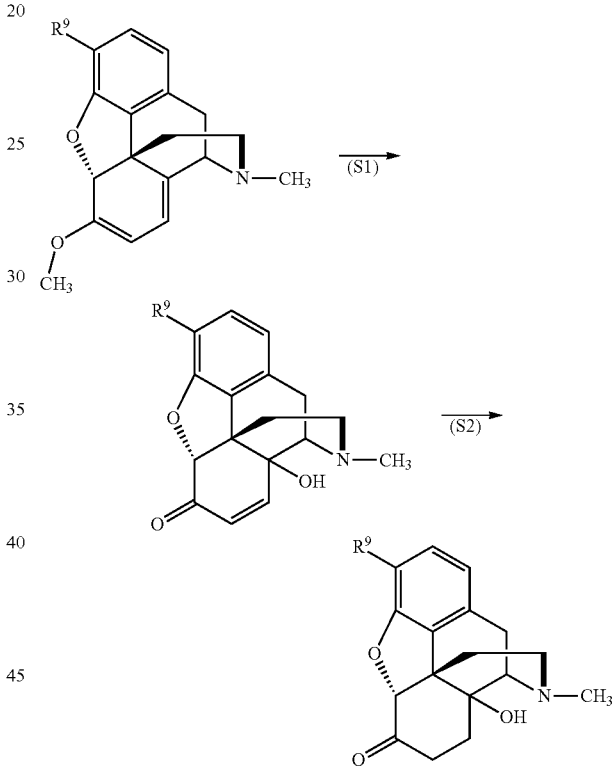

More specifically, compounds of formula (19) can be prepared by oxidizing a compound of formula (20)

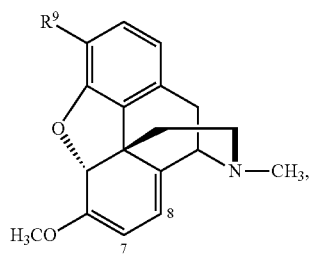

as depicted in step (S1) of Scheme 7 to provide a compound of formula (21)

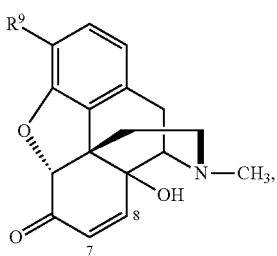

and hydrogenating the 7,8-double bond of the compound of formula (21) in step (S2) of Scheme 7 to provide the compound of formula (19), where $R^9$ is selected from the group consisting of —OH, —H, and —OR$^{15}$, where $R^{15}$ is an oxygen protecting group.

In certain embodiments, $R^9$ is —OH, and therefore the compound of formula (20) is oripavine. In another embodiment, $R^9$ is —OCH$_3$ and the compound of formula (20) is thebaine.

In certain embodiments, step (S1) of Scheme 7 (oxidation) is carried out by contacting the compound of formula (20) with a peroxyacid such as peracetic acid, performic acid, or m-chlorperbenzoic acid. The peroxy acid can be formed in situ, for example by addition of hydrogen peroxide to acetic acid or to formic acid, to provide the oxidized compound of formula (21). In step (S2) of Scheme 7, the compound of formula (21) is hydrogenated to provide the compound of formula (19). Hydrogenation can be carried out, for example, by contact with hydrogen gas in the presence of a precious metal catalyst such as Pd/C or Pt/C using conditions and reagents disclosed in the following references, each of which is hereby incorporated by reference in its entirety: Krassnig et al. (1996) *Arch. Pharm. Med. Chem.* 329:325-326; U.S. Pat. No. 5,112,975 to Wallace; U.S. Pat. No. 4,472,253 to Schwartz; and U.S. Pat. Nos. 1,485,673 and 1,468,805 to Freund et al. In other embodiments, the 7,8-double bond of the compound of formula (21) is subjected to transfer hydrogenation to provide the compounds of formula (19), e.g., according to methods disclosed in WO 2005/097801 A1; U.S. Pat. No. 6,177,567 B1; WO 2006/094672 A1; Rao (1982) *J. Org. Chem.* 47:369-371; and Fahrenholtz (1972) *J. Org. Chem.* 37(13):2204-2207.

In certain embodiments, the reactions of Scheme 7 are combined with those of Scheme 4 to provide a process for conversion of compounds of formula (20) to the carbamate derivatives of formula (7).

In other embodiments, the reactions of Scheme 7 are combined with those of Scheme 5 to provide a process for conversion of compounds of formula (20) to the secondary amine, or "nor" derivatives, of formula (8). In one embodiment therefore the present disclosure provides a process for conversion of a compound of formula (20), in which $R^9$ is —OH, to a compound of formula (7), i.e., a process for the preparation of noroxymorphone from oripavine.

In certain embodiments, the reactions of Scheme 7 are combined with those of Scheme 6 to provide a process for conversion of compounds of formula (20) to the compounds of formula (9). In one embodiment therefore the present disclosure provides a process for conversion of a compound of formula (20), in which $R^9$ is —OH, to a compound of formula (9) in which $R^{16}$ is allyl, i.e., a process for the preparation of naloxone from oripavine. In another embodiment, the present disclosure also provides a process for conversion of a compound of formula (20), in which $R^9$ is —OH, to a compound of formula (9) in which $R^{16}$ is methylcyclopropyl, i.e., a process for the preparation of naltrexone from oripavine.

In certain embodiments, the processes obtained by combining the reactions of Scheme 7 with those of any of Schemes 4, 5, and 6 are "one pot" processes that are carried out without chromatographic isolation of the intermediate compounds.

4.7 Process for the Preparation of Noroxymorphone from Oxymorphone

In a specific embodiment, the present disclosure provides a process for the conversion of oxymorphone to noroxymorphone, as depicted in Scheme 8.

Scheme 8

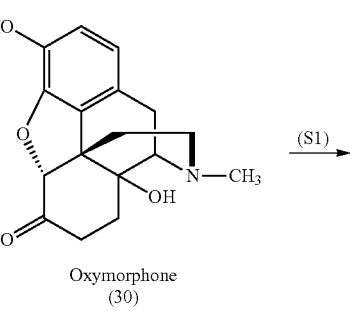

Oxymorphone
(30)

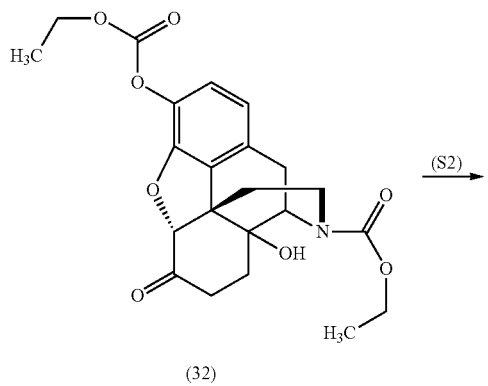

(32)

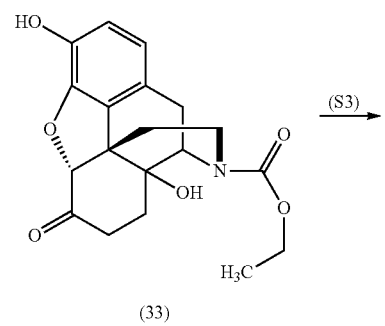

(33)

-continued

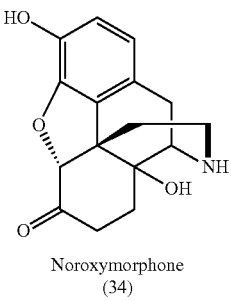

Noroxymorphone
(34)

In one embodiment, oxymorphone is taken up in a tertiary alcohol, e.g., tert-amyl alcohol, and sodium bicarbonate and sodium iodide are added. The resulting mixture is subjected to azeotropic distillation, removing water that might be present. The dried mixture is incubated at a temperature of 80° C.-85° C. and excess ethyl chloroformate (compound (42)) is added in portions. The major product of step (S1) is the 3-carbonate-17-carbamate bis-protected molecule, compound (32). Surprisingly, the anticipated carbonate that would be produced by reaction between the alcohol solvent and the chloroformate reagent was not observed. Once step (S1) is complete, water and sodium carbonate are added and the resulting biphasic mixture heated at a temperature of 80° C.-85° C. (step (S2)) to eliminate unreacted chloroformate reagent and to convert the 3-carbonate moiety to the free hydroxy, providing the carbamate derivative, compound (33).

After cleavage of the 3-carbonate moiety, the mixture comprising the carbamate derivative, compound (33), is cooled to a temperature of about 20° C.-40° C., the pH adjusted to a pH of from about pH 1 to about pH 2 with concentrated acid, e.g., hydrochloric acid or sulfuric acid, and the aqueous layer removed. The organic layer is washed with aqueous sodium bisulfate, and the aqueous layer removed by phase-cut separation. Water is added to the washed organic layer and the mixture is distilled under atmospheric pressure at a temperature within the range of from about 80° C. to about 100° C., thereby removing the tert-amyl alcohol as an azeotrope with water, yielding the carbamate derivate, compound (33), as an aqueous suspension (slurry). The end-point of the distillation is determined by measurement of residual tert-amyl alcohol using gas chromatography. In step (S3) of Scheme 8, sulfuric acid is added to the slurry at a temperature of less than or equal to about 100° C., and the hydrolysis continued at a temperature of at least 95° C. until conversion of the carbamate, compound (33), to noroxymorphone, compound (34), is complete.

The reaction mixture is diluted with water, cooled to a temperature within the range of from about 10° C. to about 20° C. and its pH adjusted within the range of from about pH 1 to about pH 2 with base, e.g., concentrated ammonium hydroxide, at a temperature within the range of from about 10° C. to about 20° C., i.e., at a temperature below about 20° C. The mixture is filtered and the pH of the filtrate adjusted within the range of from about pH 8.8 to about pH 9.1 with base, e.g., concentrated ammonium hydroxide. The resulting solid suspension is cooled to a temperature of 0° C.-5° C. and filtered. The collected solids are washed with water and then washed with methanol, and dried under reduced pressure at elevated temperature (e.g., 105° C.) to provide noroxymorphone, compound (34).

4.8 Process for the Preparation of Naloxone and Naltrexone from Oxymorphone

In another embodiment, the present disclosure provides processes for the conversion of oxymorphone to naloxone and for the conversion of oxymorphone to naltrexone, as depicted in Scheme 9.

Scheme 9

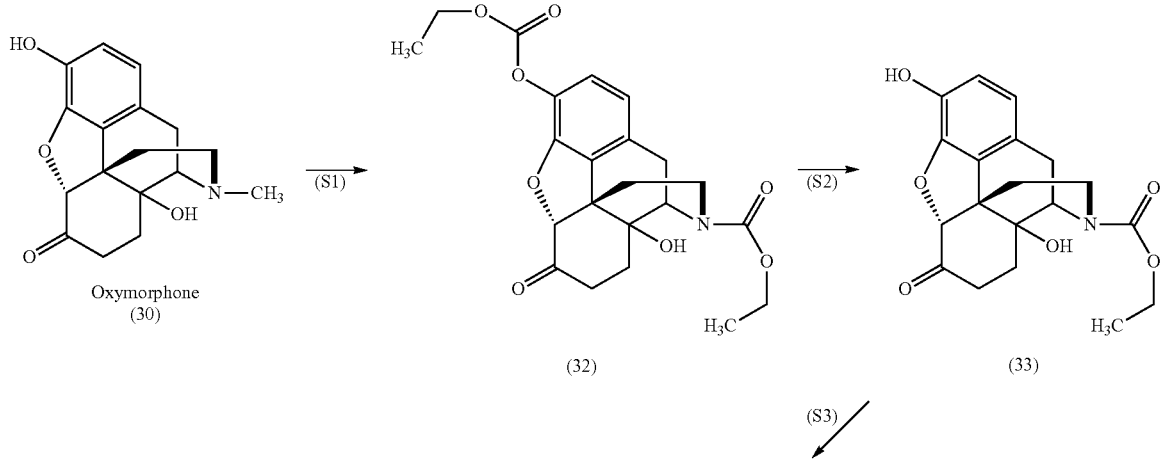

-continued

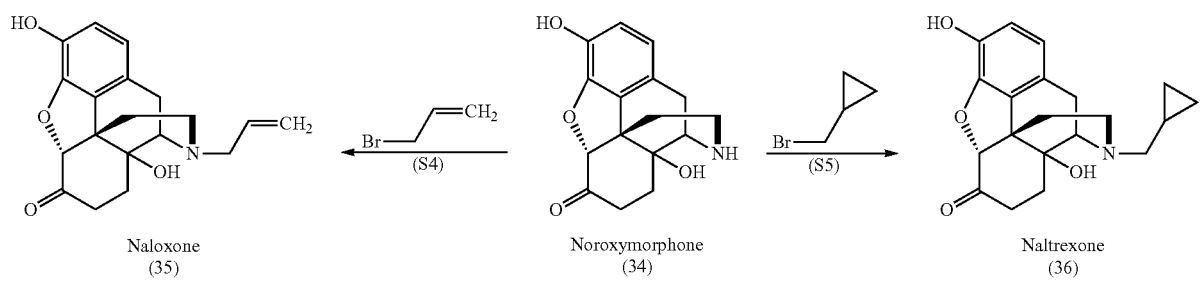

Steps (S1)-(S3) of Scheme 9 are as described for the corresponding reactions of Scheme 8. In step (S4) of Scheme 9, noroxymorphone prepared as described above is taken up in a solvent, e.g., ethanol or dimethyl formamide, to which sodium bicarbonate, sodium iodide, and ally bromide are added. The mixture is heated to a temperature of about 70° C. and the reaction allowed to proceed until deemed complete. The pH is adjusted with hydrochloric acid and naloxone is isolated as the hydrochloride salt. In a similar manner, in step (S5) of Scheme 9, noroxymorphone prepared as described above is taken up in a solvent, e.g., ethanol or dimethyl formamide, to which sodium bicarbonate, sodium iodide, and cyclopropylmethyl bromide are added. The mixture is heated to a temperature of about 70° C. and the reaction allowed to proceed until deemed complete. The pH is adjusted with hydrochloric acid and naltrexone is isolated as the hydrochloride salt.

In certain embodiments, either or both of steps (S1) and (S4) of Scheme 9 are carried out in the presence of an iodide salt. In certain embodiments, either or both of steps (S1) and (S5) of Scheme 9 are carried out in the presence of an iodide salt. In certain embodiments, the iodide salt is present in a sub-stoichiometric amount. In certain embodiments, the iodide salt is present in a catalytic amount.

4.9 Process for the Preparation of Noroxymorphone, Naloxone, and Naltrexone from Oripavine In another embodiment, the present disclosure provides processes for the conversion of oripavine to noroxymorphone, naloxone, and naltrexone as depicted in Scheme 10.

Scheme 10

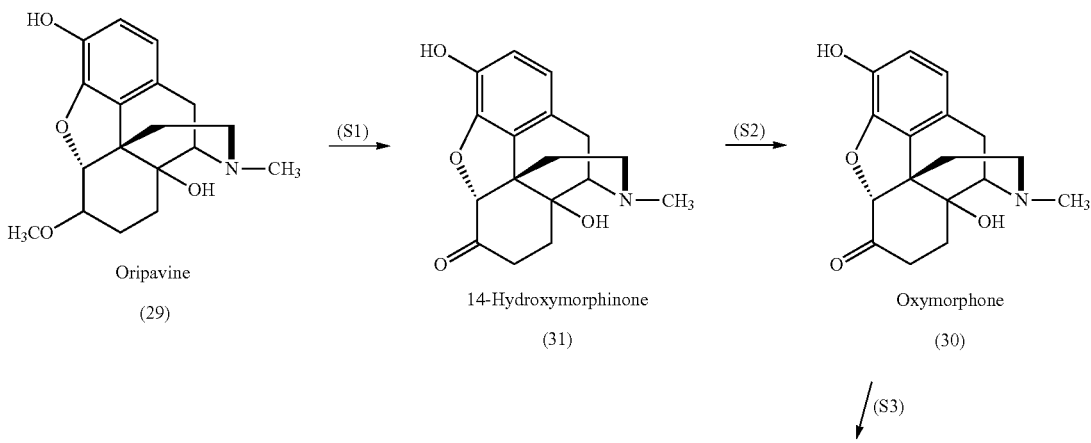

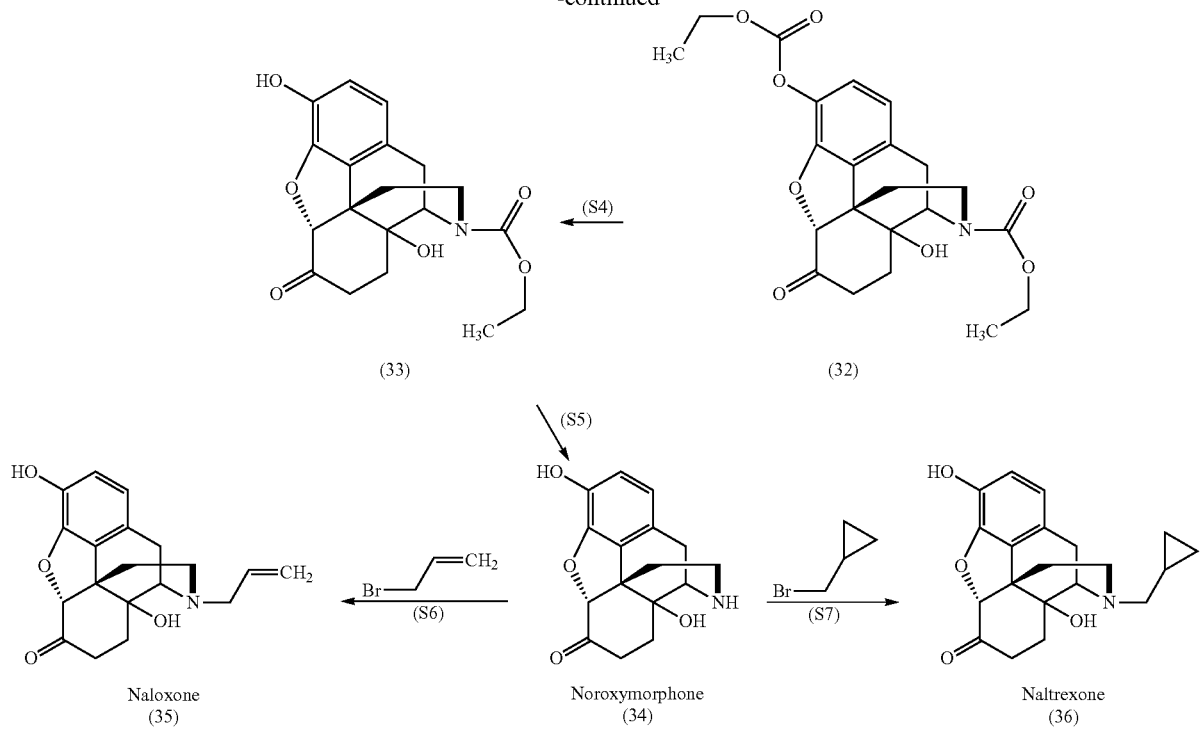

In step (S1) of Scheme 10, the natural product oripavine is oxidized, in one embodiment with a peroxy acid, to the 14-hydroxy-6-keto-Δ$^7$-double bond containing derivative 14-hydroxymorphinone, compound (31). In another embodiment, oripavine is oxidized with m-chloroperbenzoic acid in a solvent comprising a mixture of acetic acid and trifluoroacetic acid. In a further embodiment, oripavine is oxidized with hydrogen peroxide in a solvent comprising acetic acid or formic acid. In certain embodiments, oripavine is dissolved in water, formic acid and hydrogen peroxide are added, and the mixture heated until oxidation is complete.

Step (S2), hydrogenation of the Δ$^7$-double bond (7,8-double bond), can be performed without isolation of the 14-hydroxymorphinone product, compound (31), which is the product of step (S1) of Scheme 10. In one embodiment, a catalyst is added directly to the oxidation reaction mixture upon completion of step (S1) of Scheme 10, the resulting mixture is swept with an inert gas, subjected to reduced pressure, and then the reaction vessel is pressurized with hydrogen gas. The hydrogenation (step (S2) of Scheme 10) is carried out at elevated temperature, e.g., 40° C. to 45° C., until the reaction is complete. In certain embodiments of this reaction, the catalyst is a metal catalyst which can be selected from among homogeneous and heterogeneous platinum, palladium, rhodium, and ruthenium catalysts. In a particular embodiment, the catalyst is a carbon-supported palladium (Pd/C) catalyst.

In one embodiment, the hydrogenation reaction mixture is cooled to a temperature of from about 2° C. to about 10° C. and filtered to remove the catalyst. The pH of the filtrate is then adjusted with base, e.g., sodium hydroxide, to about pH 9 and the product, crude oxymorphone, is collected by filtration and washed with water. In one embodiment, the crude oxymorphone is dried under reduced pressure at elevated temperature, e.g., 105° C., before proceeding to the next step. In one embodiment, the crude oxymorphone is used as the wet-cake without drying. That is, the product of the hydrogenation reaction, oxymorphone (compound (30)), need not be dried before proceeding to step (S3) of Scheme 10. The remaining steps of Scheme 10 (steps (S3)-(S7)) correspond to steps (S1)-(S5) of Scheme 9, respectively.

4.10 Process for the Preparation of Compounds of Formulae (11) and (15)

In other illustrative embodiments, the present disclosure provides methods for the synthesis of compounds of formula (11) and formula (15). More specifically, the present disclosure provides a method for making a compound of formula (11)

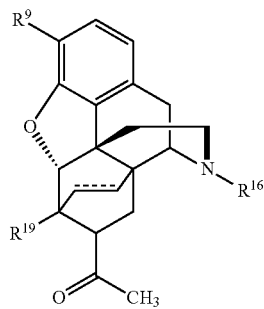

comprising (a) contacting a compound of formula (12)

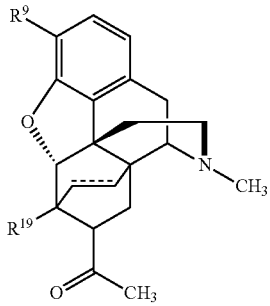

with a compound of formula (2)

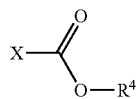

in a solvent to provide a compound of formula (13)

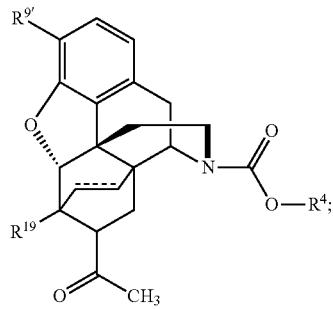

(b) converting the compound of formula (13) to a compound of formula (14)

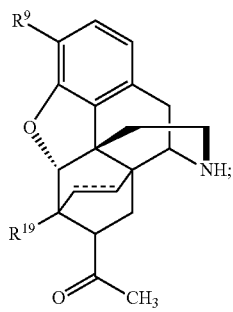

and (c) contacting the compound of formula (14) with a compound of formula (10) $X^1$—$R^{16}$ to provide the compound of formula (11), wherein the ----- bond is a single bond or a double bond, and the solvent comprises a tertiary alcohol. $R^4$, $R^9$, $R^{9'}$, $R^{16}$, $R^{19}$, and X are as defined above.

In certain embodiments, the solvent is a tertiary alcohol or consists essentially of a tertiary alcohol. The tertiary alcohol is a compound of formula (5)

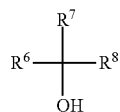

in which $R^6$, $R^7$, and $R^8$ are each independently —($C_1$-$C_6$) alkyl. In certain embodiments of this method, the tertiary alcohol is selected from the group consisting of tert-amyl alcohol, tert-butyl alcohol, 3-methyl-3-pentanol, 2,3-dimethyl-3-pentanol, 3-ethyl-3-pentanol, 2-methyl-2-hexanol, and mixtures of two or more thereof. In a particular embodiment, the tertiary alcohol is tert-amyl alcohol.

In certain embodiments, conversion of the compound of formula (13) to the compound of formula (14) comprises contacting the compound of formula (13) with a base to provide the compound of formula (14). In certain embodiments, the base is selected from the group consisting of $Na_2CO_3$, $K_2CO_3$, $Cs_2CO_3$, $Na_3PO_4$, $Na_2HPO_4$, and combinations of two or more thereof. In a particular embodiment, the base is $Na_2CO_3$.

The present disclosure also provides a method for making a compound of formula (15)

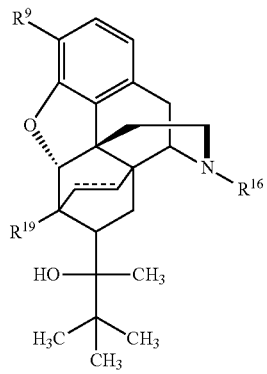

comprising (a) contacting the compound of formula (16)

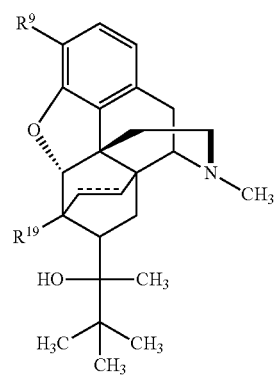

with a compound of formula (2)

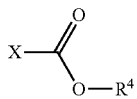

in a solvent to provide a compound of formula (17)

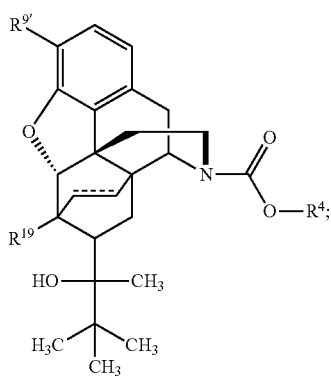

(b) converting the compound of formula (17) to a compound of formula (18)

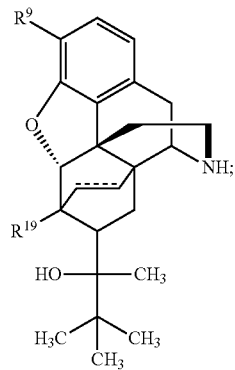

and (c) contacting the compound of formula (18) with a compound of formula (10) X'—$R^{16}$ to provide the compound of formula (15), where the solvent comprises a tertiary alcohol. The ----- bond is a single bond or a double bond. $R^4$, $R^9$, $R^{9'}$, $R^{16}$, $R^{19}$, X, and X' are as defined above.

In certain embodiments, the solvent is a tertiary alcohol or consists essentially of a tertiary alcohol. The tertiary alcohol is a compound of formula (5)

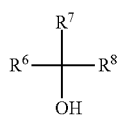

wherein $R^6$, $R^7$, and $R^8$ are each independently —($C_1$-$C_6$) alkyl. The tertiary alcohol therefore can be selected from the group consisting of tert-amyl alcohol, tert-butyl alcohol, 3-methyl-3-pentanol, 2,3-dimethyl-3-pentanol, 3-ethyl-3-pentanol, 2-methyl-2-hexanol, and mixtures of two or more thereof. In certain embodiments, the tertiary alcohol is tert-amyl alcohol.

In certain embodiments of these methods for making compounds of formula (11) and formula (15), $R^{16}$ is methylcyclopropyl, the ----- bond is a single bond, $R^9$ is —OH, and $R^{19}$ is —$OCH_3$.

In certain embodiments of these methods for making compounds of formula (11) and formula (15), each oxygen protecting group, $R^{15}$, can be independently selected from the group defined previously.

In certain embodiments of these methods for making compounds of formula (11) and formula (15), $R^9$ is —$OR^{15}$ and $R^{15}$ is —$C(O)OR^{18}$. In particular embodiments of these methods, $R^{18}$ is iso-butyl. In other particular embodiments of these methods, $R^{18}$ is ethyl.

In certain embodiments of these methods for making compounds of formula (11) and formula (15), step (a) in each instance can be carried out in the presence of an iodide salt. In certain embodiments, the iodide salt is present in a substoichiometric amount. In certain embodiments, the iodide salt is present in a catalytic amount. The iodide salt can be selected from the group consisting of NaI, KI, LiI, CsI, RuI, $MgI_2$, $CaI_2$, $NH_4I$, tetrabutylammonium iodide, and combinations of two or more thereof, and in particular embodiments, the iodide salt is NaI.

In certain embodiments of these methods for making compounds of formula (11) and formula (15), step (c) in each instance can be carried out in the presence of an iodide salt. In certain embodiments, the iodide salt is present in a substoichiometric amount. In certain embodiments, the iodide salt is present in a catalytic amount. The iodide salt can be selected from the group consisting of NaI, KI, LiI, CsI, RuI, $MgI_2$, $CaI_2$, $NH_4I$, tetrabutylammonium iodide, and combinations of two or more thereof, and in particular embodiments, the iodide salt is NaI.

4.11 Processes for the N-Dealkylation of Natural Products

In one embodiment, the methods disclosed herein are also useful in processes for the synthesis of the potent dopamine receptor agonist, cabergoline (compound (37)).

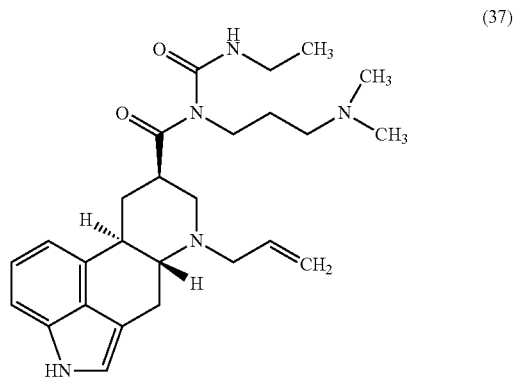 [SMILES: C=CCN1C[C@H](C(=O)N(CCCN(C)C)C(=O)NCC)C[C@@H]2c3cccc4[nH]cc(c34)C[C@H]21]

These processes involve the conversion of the tertiary amine of either lysergol (compound (38)) or elymoclavine (compound (40)) to the N-allyl group of cabergoline, using the reagents and methods disclosed herein.

Scheme 11

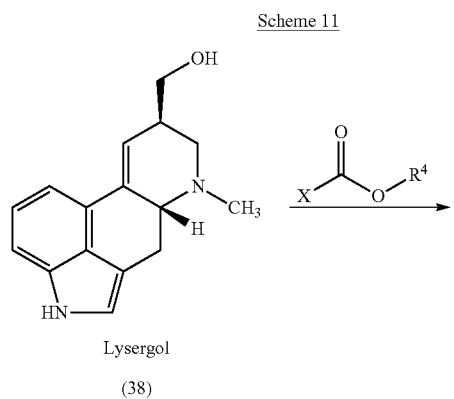

Lysergol
(38)

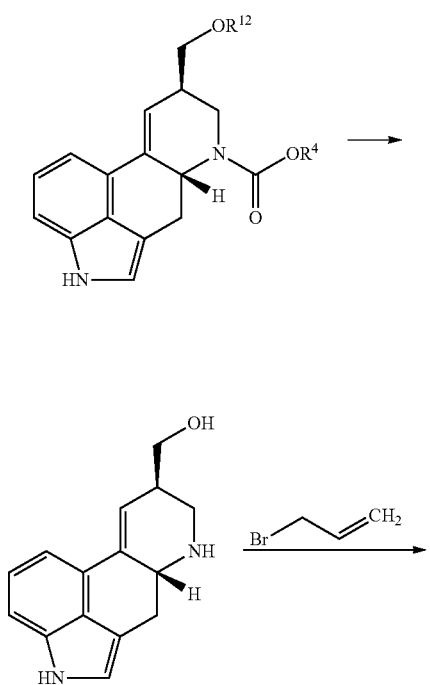

(39)

Scheme 12

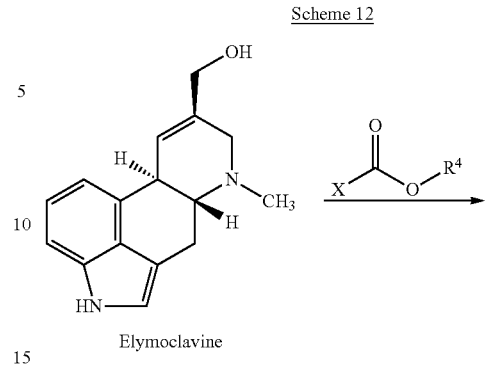

Elymoclavine
(40)

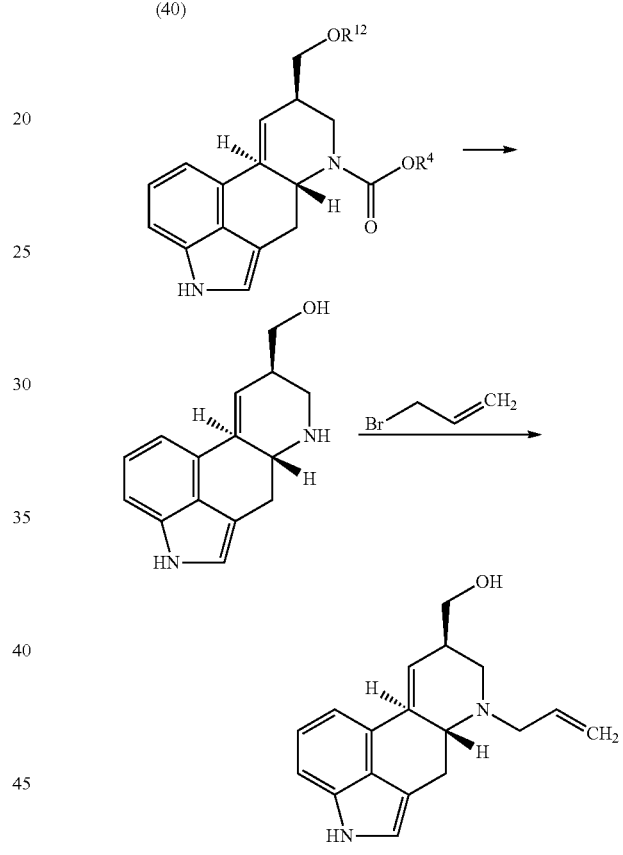

(41)

In certain embodiments therefore the starting material—either lysergol (compound (38)) or elymoclavine (compound (40))—is demethylated by contacting with a haloformate reagent to provide the corresponding carbamate derivative where, as discussed above, $R^{12}$ can be either —H or —C(O)OR$^4$. The carbamate derivatives can be hydrolyzed to provide the secondary amines ("nor" derivatives) depicted in Schemes 11 and 12, which, in turn, can be contacted with allyl bromide to provide the intermediates, i.e., compounds (39) and (41). The methanol group may react with the allyl haloformate reagent, converting the hydroxy group to a carbonate derivative moiety, which can be converted to the free hydroxy using methods disclosed herein, e.g., by including a base treatment step (see, e.g., step (S2) of Scheme 9 above).

In other aspects of this embodiment, lysergol or elymoclavine are first hydrogenated to provide the piperidine derivatives depicted below before formation of the N-allyl derivatives thereof, as depicted in Schemes 13 and 14 respectively, where $R^{12}$ is as defined above.

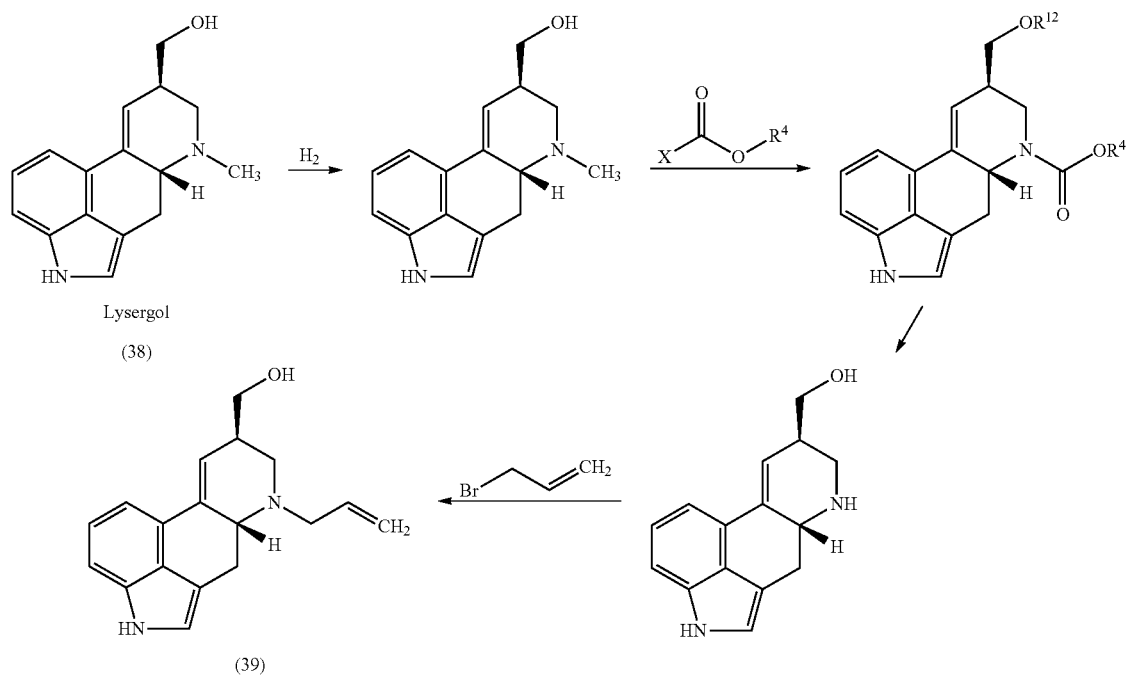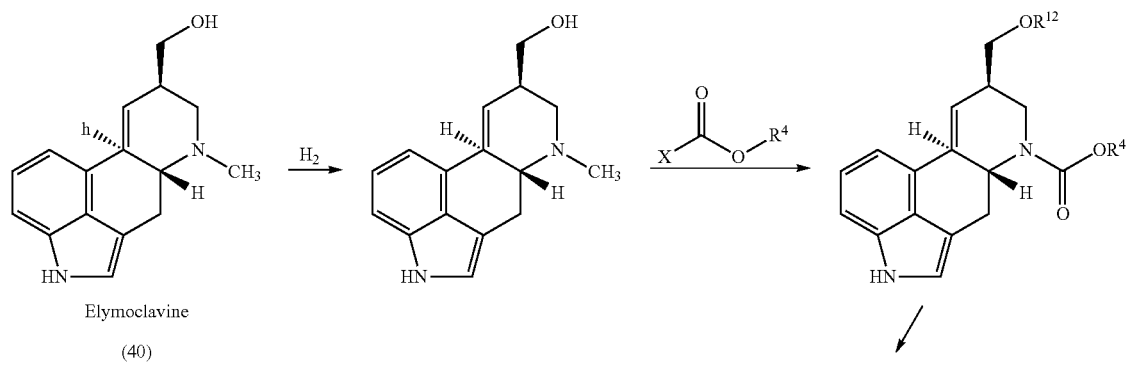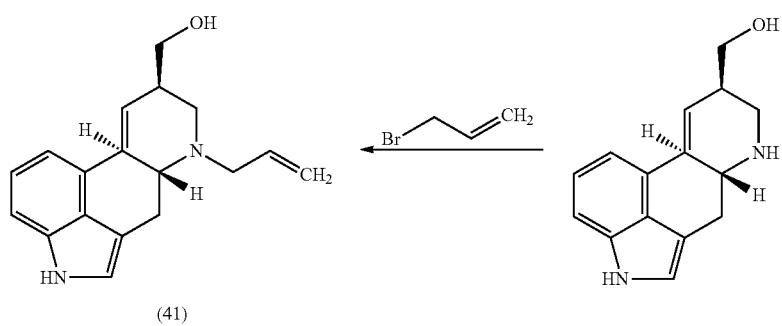

Conditions for hydrogenation of lysergol or elymoclavine and the additional reactions for conversion of the N-allyl derivative disclosed above to the final product can be found in U.S. Patent Application Publication No. US 2008/0275240 A1 and U.S. Pat. No. 7,217,822 B2, each of which is hereby incorporated by reference in its entirety.

In certain other illustrative embodiments, the methods disclosed are used for converting the following tertiary amines to the corresponding secondary amines or "nor" derivatives: atropine, cabergoline, caffeine, (+)-eschscholtzidine, galanthamine, and nicotine, according to Schemes 15-19.

Scheme 15: Atropine

Scheme 16: Caffeine

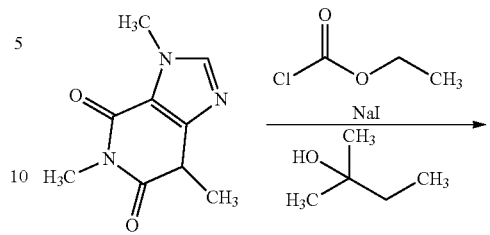

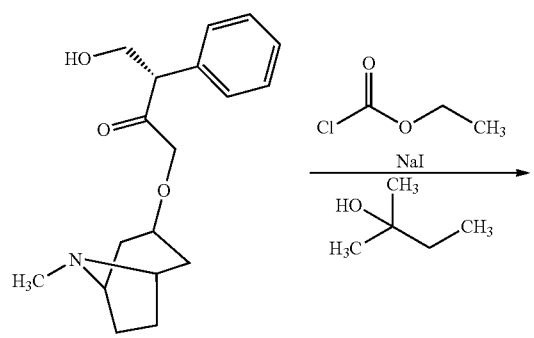

Scheme 17: (+)-Eschscholtzidine

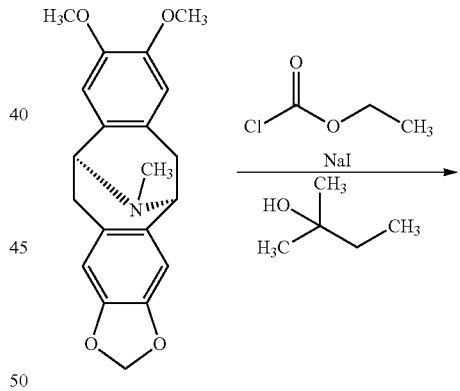

Scheme 18: Galanthamine

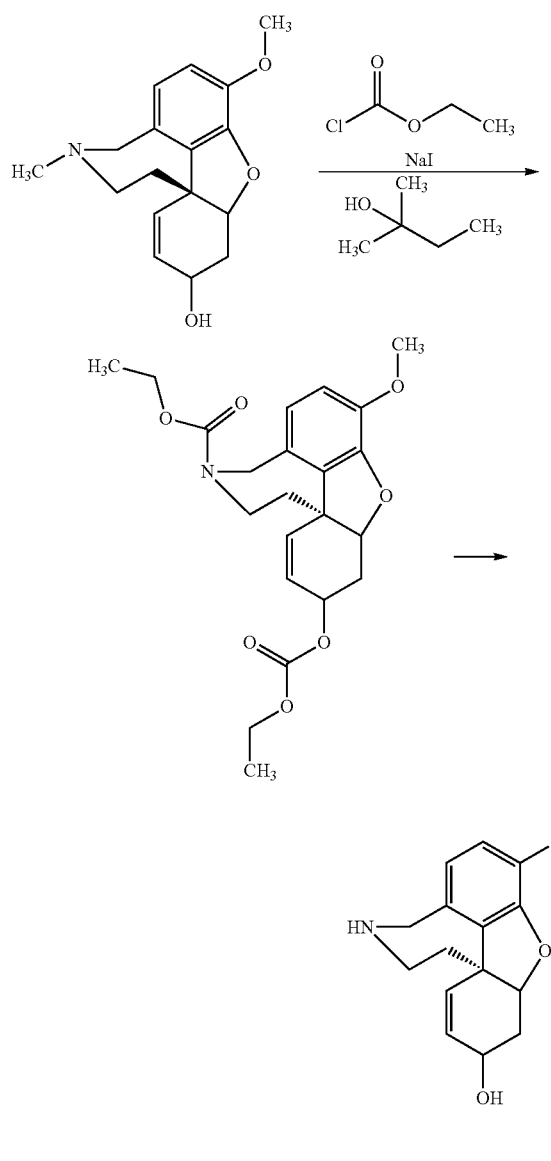

Scheme 19: Nicotine

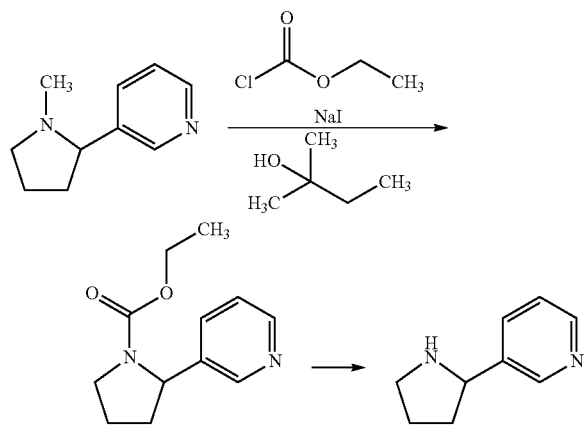

As depicted in each of these schemes, each compound (atropine, caffeine, (+)-eschscholtzidine, galanthamine, and nicotine) is taken up in tert-amyl alcohol and contacted with a haloformate reagent (ethyl chloroformate) in the presence of a catalytic amount of an iodide salt (NaI) to provide the carbamate intermediate depicted. Hydrolysis of the carbamate, typically with a mineral acid (e.g., sulfuric acid or hydrochloric acid) or a base, provides the demethylated secondary amine, or "nor" derivative, of each compound.

4.12 Compositions

The present disclosure also provides a composition prepared by combining a compound of formula (1),

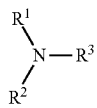

a compound of formula (2)

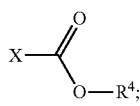

and a tertiary alcohol, in which $R^1$, $R^2$, and $R^3$ are as previously defined above.

$R^4$ is as previously defined above.

The present disclosure further provides a composition prepared by combining a compound of formula (6)

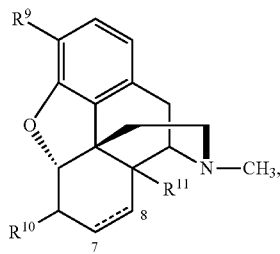

a compound of formula (2)

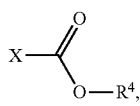

and a tertiary alcohol. The ----- 7,8-bond is a single bond or a double bond, and $R^9$ and $R^{11}$ are each independently selected from the group consisting of —OH, —H, and —OR$^{15}$, where $R^{15}$ is an oxygen protecting group. $R^{10}$ is selected from the group consisting of =O, =CH$_2$, —H, and —OR$^{15}$.

$R^4$ is selected from the group consisting of —(C$_1$-C$_6$)alkyl, —(C$_2$-C$_6$)alkenyl, —(C$_2$-C$_6$)alkynyl, aryl, and heteroaryl, each being unsubstituted or substituted with 1, 2, 3, 4, or 5 independently-selected $R^5$ groups, and each $R^5$ is independently selected from the group consisting of —OH, —Cl, —Br, —I, —NH₂, —CN, —O—(C₁-C₆)alkyl, and phenyl. X is selected from the group consisting of —Cl, —Br, —I, mesylate, and tosylate.

In another embodiment, the present disclosure provides a composition prepared by combining a compound of formula (12)

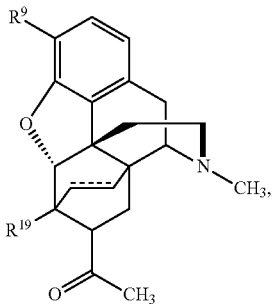

a compound of formula (2)

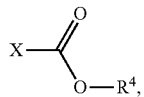

and a tertiary alcohol. The ------ bond is a single bond or a double bond, and $R^9$ is selected from the group consisting of —OH, —H, and —OR$^{15}$, where $R^{15}$ is an oxygen protecting group. $R^{19}$ is selected from the group consisting of —H, —OH, —CH₃, and —OR$^{15}$.

$R^4$ is as previously defined above.

In a still further embodiment, the present disclosure also provides a composition prepared by combining a compound of formula (16)

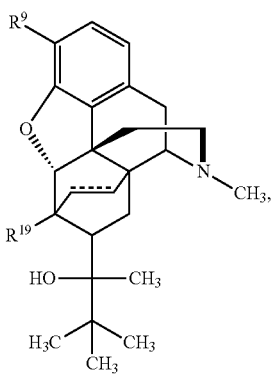

a compound of formula (2)

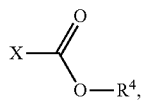

and a tertiary alcohol, each as previously defined above.

The following examples are set forth to assist in understanding the invention and should not be construed as specifically limiting the invention described and claimed herein. Such variations of the invention, including the substitution of all equivalents now known or later developed, that would be within the purview of those skilled in the art, and changes in formulation or changes in experimental design, are to be considered to fall within the scope of the invention incorporated herein.

5. EXAMPLES

The reactions and processes of the present disclosure are described in more detail below.

Example 1

Preparation of Noroxymorphone from Oxymorphone

In one illustrative embodiment, oxymorphone is converted to noroxymorphone in a process that comprises heating a suspension of oxymorphone (compound (30)), NaHCO₃, and sodium iodide in tert-amyl alcohol to a temperature of 80° C., followed by slow addition of ethyl chloroformate (compound (42)). This provides the bis-protected material (compound (32)) (>95% purity by HPLC area %). After the demethylation is complete (>95% conversion), compound (32) is hydrolyzed after addition of water and Na₂CO₃ to provide the N-carbamate product (compound (33), >98% purity by HPLC area %). After acidification, the aqueous layer containing unreacted oxymorphone and other impurities is removed. After two additional aqueous acidic washes, the organic layer comprises approximately 30% w/w of compound (33) in tert-amyl alcohol. Addition of water to this solution, followed by removal of tert-amyl alcohol by distillation of its azeotrope with water at a temperature of 85° C., yields compound (33) as a suspension in water. After addition of sulfuric acid, compound (33) is hydrolyzed at elevated temperatures. Noroxymorphone (compound (34)) is then isolated after basification.

In certain embodiments, the N-demethylation of oxymorphone can be incorporated within an overall process for the synthesis of naloxone or naltrexone from a natural product, e.g., oripavine (compound (29)). These reactions and processes are described in more detail below.

Example 2

Synthesis of Oxymorphone from Oripavine

Oripavine (compound (29)) is dissolved (in portions) in a mixture comprising 4.3 volumes of water, 28 equivalents of 88% formic acid, and 1.1 equivalents of hydrogen peroxide. The resulting mixture is stirred at a temperature of 45° C. for four hours. Once the oxidation reaction is complete, 5% Pd/C is added directly to that reaction mixture to a level of 0.8%. The reaction mixture is first swept with dry nitrogen (40-45 psi) after which reduced pressure is applied, and then the vessel is pressurized with hydrogen gas (40-45 psi) at a temperature of from 40° C. to 45° C. Once the hydrogenation reaction is complete, the reaction mixture is cooled to a temperature of from 2° C. to 10° C., filtered to remove the catalyst, and adjusted to about pH 9 with 50% sodium hydroxide. The crude oxymorphone free base is then collected by filtration, washed with water (about three volumes), and dried under reduced pressure at a temperature of 105° C. The crude product is at least 94% oxymorphone as determined by HPLC area %.

Example 3

Synthesis of Noroxymorphone from Oxymorphone

Crude oxymorphone (as prepared in Example 2), which may contain residual water and ethanol, is resuspended in tert-amyl alcohol (7.5 L per Kg oxymorphone) and dried by azeotropic distillation. The resulting dried oxymorphone solution is treated with a three-fold molar excess of ethyl chloroformate in the presence of 30 mol % sodium iodide and a three-fold molar excess of sodium bicarbonate at a temperature of from 80° C. to 85° C. until the reaction is complete (about four hours). Water (3.5 L per Kg oxymorphone) and sodium carbonate (1.2-fold molar excess) are added and the resulting mixture is heated at a temperature of from 80° C. to 85° C. for at least fifteen hours to destroy residual ethyl chloroformate and hydrolyze the 3-carbonate moiety to the corresponding 3-hydroxy, yielding the 17-carbamate intermediate. This mixture is cooled to a temperature of from 20° C. to 40° C., adjusted to a pH within the range of from about pH 1 to about pH 2 with concentrated hydrochloric acid or sulfuric acid, and the aqueous layer removed by phase-cut separation. The upper tert-amyl alcohol layer is washed twice with aqueous 25% sodium bisulfate (3.5 L). After the second wash is removed by phase-cut separation, water (three volumes) is added to the organic (tert-amyl alcohol) layer. The tert-amyl alcohol is removed by azeotropic distillation at temperature of from 80° C. to 100° C. at atmospheric pressure, with the end point determined by measuring residual tert-amyl alcohol in the aqueous slurry by GC. The volume of water is adjusted back to three volumes by adding water to replace that removed during distillation.

Sulfuric acid is added to the resulting aqueous slurry at a temperature≤100° C. and hydrolysis continues at a temperature>95° C. until conversion of the carbamate moiety to the secondary amine is complete. The mixture is then diluted with three volumes of water, cooled to a temperature of about 15° C. (within the range of from 10° C. to 20° C.), and adjusted to a pH within the range of from about pH 1 to about pH 2 with 28-30% ammonium hydroxide at a temperature below about 20° C. The solution is filtered and the filtrate is adjusted to a pH within the range of from about pH 8.8 to about pH 9.1 with 28-30% ammonium hydroxide at a temperature below about 20° C. The resulting suspension is cooled to a temperature of from 0° C. to 5° C. and filtered. The collected solids are washed with water (3 volumes), once with three volumes of methanol, and then dried at a temperature of 105° C. under reduced pressure to provide purified crude noroxymorphone.

Example 4

Preparation of Noroxymorphone from Oxymorphone

This example illustrates a three-step "one pot" process for conversion of oxymorphone to noroxymorphone. As depicted in Scheme 20, oxymorphone (compound (30)) was N-demethylated in a tert-amyl alcohol solvent comprising NaI to provide 3,17-diethyloxycarbonyl noroxymorphone (compound (32)). Compound (32) was then hydrolyzed with base to provide compound (33) (17-ethyloxycarbonyl noroxymorphone), which, in turn was hydrolyzed with a mineral acid to provide noroxymorphone (compound (34)).

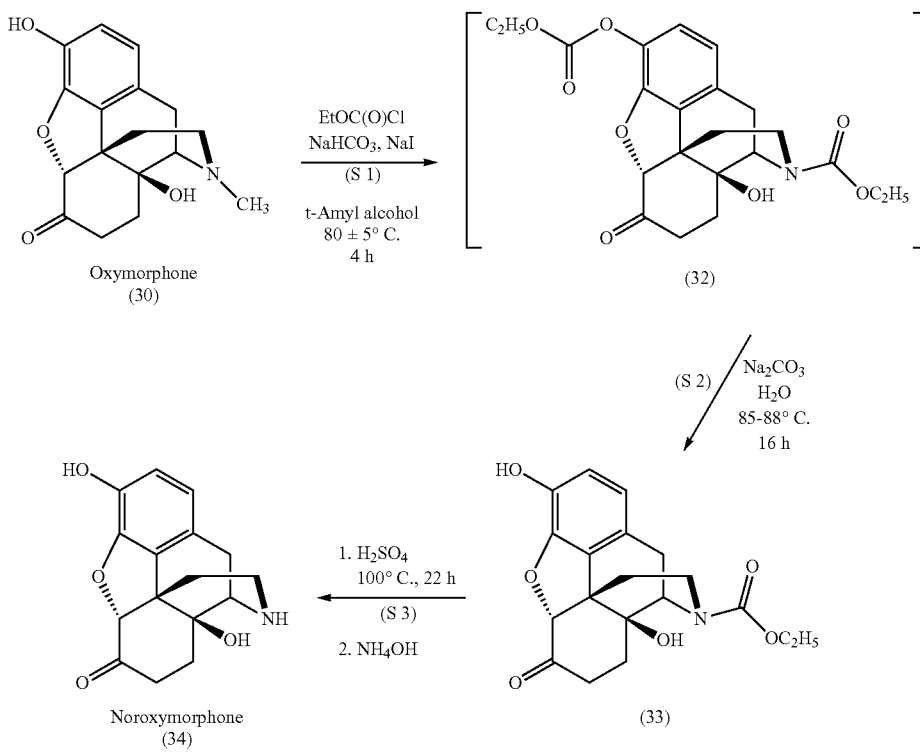

Scheme 20

In step (S1), a suspension of oxymorphone (compound (30)) (50 g, 87% w/w, 0.144 mol), sodium bicarbonate (30.32 g, 0.361 mol), and sodium iodide (12.98 g, 0.087 mol) in tert-amyl alcohol (375 mL) was heated to reflux (a temperature of about 102° C.). Approximately 200 mL of solvent (tert-amyl alcohol) was removed by distillation. The mixture was then cooled to a temperature of 80±5° C. and ethyl chloroformate (54.05 g, 0.498 mol) was added over 2 hours via a syringe pump. Upon completion of the addition, the reaction was allowed to stir at a temperature of 80±5° C. for a further 2 hours to provide compound (32) (>95% by HPLC). This mixture was used directly in step (S2), in which the 3-ethyloxycarbonyl moiety was hydrolyzed with base to provide 17-ethyloxycarbonyl noroxymorphone (compound (33)).

This mixture was then charged with water (175 mL) followed by sodium carbonate (22.95 g, 0.217 mol). The reaction was then heated to a temperature of 85-88° C. and held at this temperature for 16 hours. This provided carbamate (compound (33)) (>99% by HPLC) in a biphasic solution of tert-amyl alcohol and water. The pH of the reaction mixture was adjusted to a pH within the range of from about pH 1.5 to about pH 3.0 using sulfuric acid (98%) and the organic and aqueous layers were separated at a temperature of 45±5° C. The organic layer was then washed twice with a 25 w/w % solution of sodium bisulfate (175 mL) at a temperature of 45±5° C. To the organic layer, containing compound (33), was added water (168.80 mL) and the reaction mixture was then heated to reflux (a temperature of 85-87° C.). Most of the tert-amyl alcohol was removed by distillation (GC indicated that tert-amyl alcohol was present at <0.5 v/v %) providing compound (33) as a slurry in water. To this slurry was added any water removed during the previous distillation and the suspension was then heated to a temperature of 90 f 5° C. Compound (33) was converted to noroxymorphone (compound (34)) by acid cleavage of the 17-carbamate moiety in step (S3), as described below.

Sulfuric acid (98%, 56.23 mL, 1.055 mol) was slowly added to the aqueous slurry of compound (33) in water, ensuring that the reaction temperature remained ≤105° C. Upon completion of the reaction, the mixture was then heated to a temperature of 100±5° C. and held at this temperature for approximately 22 hours. This provided noroxymorphone (compound (34)) as a solution in about 4.5 M sulfuric acid. The reaction was then diluted with water (3 volumes), the mixture's temperature was adjusted to 50±5° C., and ammonium hydroxide (30% w/w, about 125 mL) was slowly added, keeping the temperature at about 50±5° C., until a pH within the range of from about pH 1.5 to about pH 2.0 was attained. The mixture was then filtered through a 5 μm polypropylene filter disk and the filtrate was cooled to a temperature of 25±5° C. Ammonium hydroxide (30% w/w, about 60 mL) was then added, keeping the temperature at 25±5° C., until a pH within the range of from about pH 8.8 to about pH 9.0 was reached. This mixture was then filtered (Büchner funnel) and the wet cake was slurry washed with water (200 mL), followed by a slurry wash with methanol (200 mL). The resultant wet cake was then rinsed with water (200 mL) as a replacement wash. The solid material was then dried at a temperature of 50±5° C. in an oven under reduced pressure until a loss on drying of 9-13% was achieved. This provided 41.71 g of noroxymorphone (compound (34)) as a tan to light brown solid (80% yield) with 97% purity (by HPLC area %) and an assay of 78% w/w (HPLC).

Example 5

Synthesis of Naloxone from Noroxymorphone

The purified noroxymorphone from Example 4 is combined with allyl bromide, sodium bicarbonate, and a catalytic amount of sodium iodide and heated to a temperature of 70° C. in a solvent (either ethanol or N,N-dimethylformamide) until the reaction is complete. The N-alkylated product, naloxone (compound (35)), is isolated by pH adjustment with hydrochloric acid. A final purification may also be performed by recrystallization in isopropanol/water. Alternatively, naloxone crude base is readily purified by recrystallization in toluene.

Example 6

Preparation of Buprenorphine from Oripavine

In step (1), methyl vinyl ketone (49.32 mL, 0.50 mol) was added to a slurry of oripavine (73.89 g, 0.25 mol) in isopropanol (190 mL). The mixture was heated to a temperature of 80° C. until conversion to the Diels-Alder adduct was complete as determined by HPLC analysis. The mixture was then cooled to a temperature of from about 20° C. to about 25° C. and filtered to provide 73.25 g of the Diels-Alder adduct illustrated below as a light grey solid (80% yield)

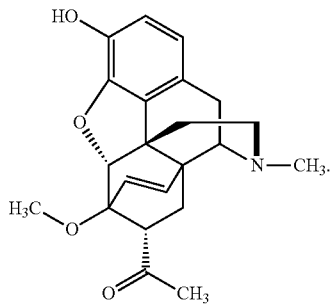

The Diels-Alder adduct (1.0 g) was suspended along with sodium bicarbonate (2.5 equivalents) and sodium iodide (0.6 equivalents) in tert-amyl alcohol (4 mL) and heated to a temperature of 80° C. Ethyl chloroformate (0.90 mL, 3.5 equivalents) was added over 1 h and the resulting reaction mixture was heated at a temperature of 80° C. until the reaction was deemed complete by HPLC analysis. The desired 3,17-bis protected product

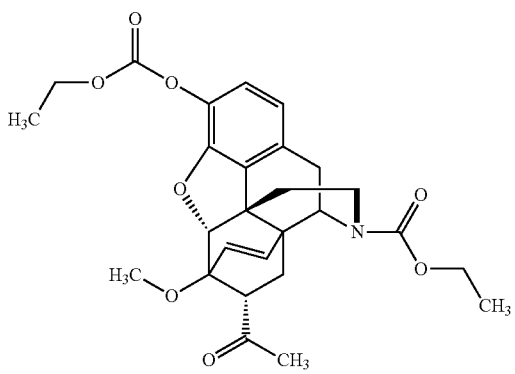

was isolated by column chromatography on silica in 67% overall yield. This material can be readily converted to the desired compound, buprenorphine, according to methods known in the art (see, e.g., WO 2009/122436 A2).

All publications, patents, patent applications, and other documents cited in this application are hereby incorporated by reference in their entireties for all purposes to the same extent as if each individual publication, patent, patent application, or other document were individually indicated to be incorporated by reference for all purposes.

While various specific embodiments have been illustrated and described, it will be appreciated that various changes can be made without departing from the spirit and scope of the invention(s).

What is claimed is:

1. A composition prepared by combining a compound of formula (12)

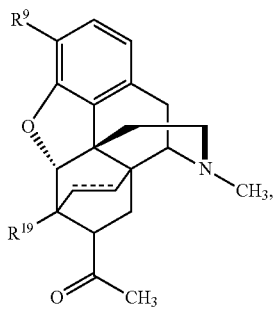

a compound of formula (2)

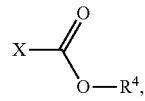

and
a tertiary alcohol;
wherein
the ----- bond is a single bond or a double bond;
$R^9$ is selected from the group consisting of —OH, —H, and —OR$^{15}$;
$R^{19}$ is selected from the group consisting of —H, —OH, —CH$_3$, and —OR$^{15}$;
$R^{15}$ is an oxygen protecting group;
$R^4$ is selected from the group consisting of —(C$_1$-C$_6$)alkyl, —(C$_2$-C$_6$)alkenyl, —(C$_2$-C$_6$)alkynyl, aryl, and heteroaryl, each being unsubstituted or substituted with 1, 2, 3, 4, or 5 independently-selected R$^5$ groups;
each $R^5$ is independently selected from the group consisting of —OH, —Cl, —Br, —I, —NH$_2$, —CN, —O—(C$_1$-C$_6$) alkyl, and phenyl; and
X is selected from the group consisting of —Cl, —Br, —I, mesylate, and tosylate.

2. The composition of claim 1, further comprising an iodide salt.

3. The composition of claim 2, wherein the iodide salt is selected from the group consisting of NaI, KI, LiI, CsI, RuI, MgI$_2$, CaI$_2$, NH$_4$I, tetrabutylammonium iodide, and combinations of two or more thereof.

4. The composition of claim 3, wherein
the oxygen protecting group is selected from the group consisting of acetyl, benzoyl, benzyl, β-methoxyethoxymethyl, dimethoxytrityl, methoxymethyl, p-methoxybenzyl, methylthiomethyl, pivaloyl, tetrahydropyranyl, trityl, trimethylsilyl, tert-butyldimethylsilyl, tert-butyldimethylsilyloxymethyl, triisopropylsilyl, —C(O)O—CH$_2$—CH=CH$_2$), tert-butyl-diphenylsilyl, tert-butyl-dimethylsilyl, tri-iso-propylsilyl, [bis-(4-methoxyphenyl)phenylmethyl)], methoxymethyl, ethoxyethyl, triphenylmethyl, —C(O)(C$_1$-C$_6$)alkyl, —C(O)OR$^{18}$, and —(C$_1$-C$_6$)alkyl, each said alkyl being unsubstituted or substituted with 1, 2, 3, 4, or 5 independently-selected R$^{50}$ groups;
each $R^{18}$ is independently selected from —(C$_1$-C$_6$)alkyl, —(C$_2$-C$_6$)alkenyl, and —(C$_2$-C$_6$)alkynyl, each said alkyl, alkenyl, and alkynyl being unsubstituted or substituted with 1, 2, 3, 4, or 5 independently-selected R$^{50}$ groups; and
each $R^{50}$ is independently selected from —Cl, —Br, —I, —NH$_2$, —CN, and phenyl.

5. The composition of claim 4, wherein R$^{16}$ is methylcyclopropyl, the ----- bond is a single bond, R$^9$ is —OH, and R$^{19}$ is —OCH$_3$.

6. A composition prepared by combining a compound of formula (16)

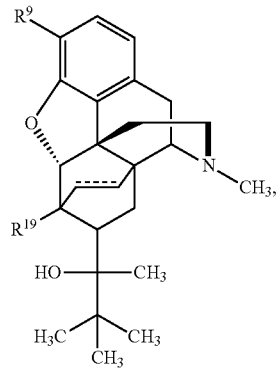

a compound of formula (2)

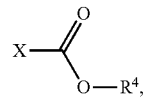

and
a tertiary alcohol;
wherein
the ----- bond is a single bond or a double bond;
$R^9$ is selected from the group consisting of —OH, —H, and —OR$^{15}$;
$R^{19}$ is selected from the group consisting of —H, —OH, —CH$_3$, and —OR$^{15}$;
$R^{15}$ is an oxygen protecting group;
$R^4$ is selected from the group consisting of —(C$_1$-C$_6$)alkyl, —(C$_2$-C$_6$)alkenyl, —(C$_2$-C$_6$)alkynyl, aryl, and heteroaryl, each being unsubstituted or substituted with 1, 2, 3, 4, or 5 independently-selected R$^5$ groups;
each $R^5$ is independently selected from the group consisting of —OH, —Cl, —Br, —I, —NH$_2$, —CN, —O—(C$_1$-C$_6$) alkyl, and phenyl; and
X is selected from the group consisting of —Cl, —Br, —I, mesylate, and tosylate.

7. The composition of claim 6, further comprising an iodide salt.

8. The composition of claim 7, wherein the iodide salt is selected from the group consisting of NaI, KI, LiI, CsI, RuI, MgI$_2$, CaI$_2$, NH$_4$I, tetrabutylammonium iodide, and combinations of two or more thereof.

9. The composition of claim 8, wherein
the oxygen protecting group is selected from the group consisting of acetyl, benzoyl, benzyl, β-methoxyethoxymethyl, dimethoxytrityl, methoxymethyl, p-methoxybenzyl, methylthiomethyl, pivaloyl, tetrahydropyranyl, trityl, trimethylsilyl, tert-butyldimethylsilyl, tert-butyldimethylsilyloxymethyl, triisopropylsilyl, —C(O)O—CH$_2$—CH=CH$_2$), tert-butyl-diphenylsilyl, tert-butyl-dimethylsilyl, tri-iso-propylsilyl, [bis-(4-methoxyphenyl)phenylmethyl)], methoxymethyl, ethoxyethyl, triphenylmethyl, —C(O)(C$_1$-C$_6$)alkyl, —C(O)OR$^{18}$, and —(C$_1$-C$_6$)alkyl, each said alkyl being unsubstituted or substituted with 1, 2, 3, 4, or 5 independently-selected R$^{50}$ groups;
each R$^{18}$ is independently selected from —(C$_1$-C$_6$)alkyl, —(C$_2$-C$_6$)alkenyl, and —(C$_2$-C$_6$)alkynyl, each said alkyl, alkenyl, and alkynyl being unsubstituted or substituted with 1, 2, 3, 4, or 5 independently-selected R$^{50}$ groups; and
each R$^{50}$ is independently selected from —Cl, —Br, —I, —NH$_2$, —CN, and phenyl.

10. The composition of claim 9, wherein R$^{16}$ is methylcyclopropyl, the ----- bond is a single bond, R$^9$ is —OH, and R$^{19}$ is —OCH$_3$.

11. A composition comprising a tertiary alcohol and a compound of formula (2)

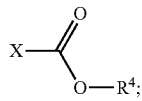

wherein
R$^4$ is selected from the group consisting of —(C$_1$-C$_6$)alkyl, —(C$_2$-C$_6$)alkenyl, —(C$_2$-C$_6$)alkynyl, aryl, and heteroaryl, each being unsubstituted or substituted with 1, 2, 3, 4, or 5 independently-selected R$^5$ groups;
each R$^5$ is independently selected from the group consisting of —OH, —Cl, —Br, —I, —NH$_2$, —CN, —O—(C$_1$-C$_6$) alkyl, and phenyl; and
X is selected from the group consisting of —Cl, —Br, —I, mesylate, and tosylate.

12. The composition of claim 11, further comprising an iodide salt.

13. The composition of claim 12, wherein the tertiary alcohol is a compound of formula (5)

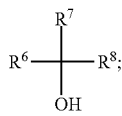

wherein R$^6$, R$^7$, and R$^8$ are each independently —(C$_1$-C$_6$) alkyl.

14. The composition of claim 13, wherein the tertiary alcohol is selected from the group consisting of tert-amyl alcohol, tert-butyl alcohol, 3-methyl-3-pentanol, 2,3-dimethyl-3-pentanol, 3-ethyl-3-pentanol, 2-methyl-2-hexanol, and mixtures of two or more thereof.

15. The composition of claim 14, wherein the tertiary alcohol is tert-amyl alcohol.

16. The composition of claim 11, further comprising a compound of formula (6)

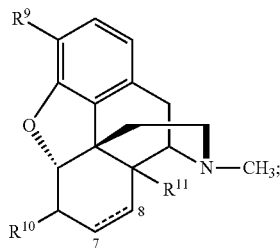

wherein
the ----- 7,8-bond is a single bond or a double bond;
R$^9$, and R$^{11}$ are each independently selected from the group consisting of —OH, —H, and —OR$^{15}$;
R$^{10}$ is selected from the group consisting of =O, —OH, =CH$_2$, —H, and —OR$^{15}$; and
R$^{15}$ is an oxygen protecting group.

17. The composition of claim 16, further comprising an iodide salt.

18. The composition of claim 17, wherein the tertiary alcohol is a compound of formula (5)

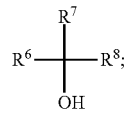

wherein R$^6$, R$^7$, and R$^8$ are each independently —(C$_1$-C$_6$) alkyl.

19. The composition of claim 18, wherein the tertiary alcohol is selected from the group consisting of tert-amyl alcohol, tert-butyl alcohol, 3-methyl-3-pentanol, 2,3-dimethyl-3-pentanol, 3-ethyl-3-pentanol, 2-methyl-2-hexanol, and mixtures of two or more thereof.

20. The composition of claim 19, wherein the tertiary alcohol is tert-amyl alcohol.

21. The composition of claim 16, wherein
the oxygen protecting group is selected from the group consisting of acetyl, benzoyl, benzyl, β-methoxyethoxymethyl, dimethoxytrityl, methoxymethyl, p-methoxybenzyl, methylthiomethyl, pivaloyl, tetrahydropyranyl, trityl, trimethylsilyl, tert-butyldimethylsilyl, tert-butyldimethylsilyloxymethyl, triisopropylsilyl, —C(O)O—CH$_2$—CH=CH$_2$), tert-butyl-diphenylsilyl, tert-butyl-dimethylsilyl, tri-iso-propylsilyl, [bis-(4-methoxyphenyl)phenylmethyl)], methoxymethyl, ethoxyethyl, triphenylmethyl, —C(O)(C$_1$-C$_6$)alkyl, —C(O)OR$^{18}$, and —(C$_1$-C$_6$)alkyl, each said alkyl being unsubstituted or substituted with 1, 2, 3, 4, or 5 independently-selected R$^{59}$ groups;
each R$^{18}$ is independently selected from —(C$_1$-C$_6$)alkyl, —(C$_2$-C$_6$)alkenyl, and —(C$_2$-C$_6$)alkynyl, each said alkyl, alkenyl, and alkynyl being unsubstituted or substituted with 1, 2, 3, 4, or 5 independently-selected R$^{59}$ groups; and
each R$^{50}$ is independently selected from —Cl, —Br, —I, —NH$_2$, —CN, and phenyl.

22. The composition of claim 21, wherein the ----- 7,8-bond is a single bond.

23. The composition of claim 22, wherein R$^9$ and R$^{11}$ are —OH and R$^{10}$ is =O.

24. The composition of claim 11, further comprising a compound of formula (12)

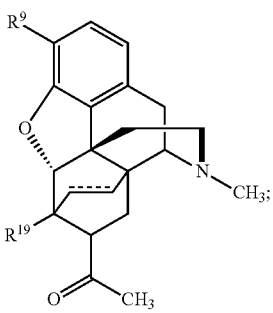

wherein
- the ----- bond is a single bond or a double bond;
- $R^9$ is selected from the group consisting of —OH, —H, and —OR$^{15}$;
- $R^{19}$ is selected from the group consisting of —H, —CH$_3$, —OH, and —OR$^{15}$; and
- $R^{15}$ is an oxygen protecting group.

25. The composition of claim 24, further comprising an iodide salt.

26. The composition of claim 25, wherein the tertiary alcohol is a compound of formula (5)

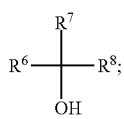

wherein $R^6$, $R^7$, and $R^8$ are each independently —(C$_1$-C$_6$) alkyl.

27. The composition of claim 26, wherein the tertiary alcohol is selected from the group consisting of tert-amyl alcohol, tert-butyl alcohol, 3-methyl-3-pentanol, 2,3-dimethyl-3-pentanol, 3-ethyl-3-pentanol, 2-methyl-2-hexanol, and mixtures of two or more thereof.

28. The composition of claim 27, wherein the tertiary alcohol is tert-amyl alcohol.

29. The composition of claim 24, wherein
the oxygen protecting group is selected from the group consisting of acetyl, benzoyl, benzyl, β-methoxyethoxymethyl, dimethoxytrityl, methoxymethyl, p-methoxybenzyl, methylthiomethyl, pivaloyl, tetrahydropyranyl, trityl, trimethylsilyl, tert-butyldimethylsilyl, tert-butyldimethylsilyloxymethyl, triisopropylsilyl, —C(O)O—CH$_2$—CH=CH$_2$), tert-butyl-diphenylsilyl, tert-butyl-dimethylsilyl, tri-iso-propylsilyl, [bis-(4-methoxyphenyl)phenylmethyl)], methoxymethyl, ethoxyethyl, triphenylmethyl, —C(O)(C$_1$-C$_6$)alkyl, —C(O)OR$^{18}$, and —(C$_1$-C$_6$)alkyl, each said alkyl being unsubstituted or substituted with 1, 2, 3, 4, or 5 independently-selected R$^{50}$ groups;
each R$^{18}$ is independently selected from —(C$_1$-C$_6$)alkyl, —(C$_2$-C$_6$)alkenyl, and —(C$_2$-C$_6$)alkynyl, each said alkyl, alkenyl, and alkynyl being unsubstituted or substituted with 1, 2, 3, 4, or 5 independently-selected R$^{50}$ groups; and
each R$^{50}$ is independently selected from —Cl, —Br, —I, —NH$_2$, —CN, and phenyl.

30. The composition of claim 29, wherein R$^{16}$ is methylcyclopropyl, the ----- bond is a single bond, R$^9$ is —OH, and R$^{19}$ is —OCH$_3$.

31. The composition of claim 11, further comprising a compound of formula (16)

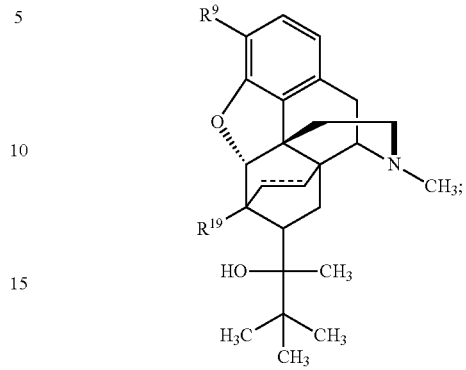

wherein
- the ----- bond is a single bond or a double bond;
- $R^9$ is selected from the group consisting of —OH, —H, and —OR$^{15}$;
- $R^{19}$ is selected from the group consisting of —H, —OH, —CH$_3$, and —OR$^{15}$; and
- $R^{15}$ is an oxygen protecting group.

32. The composition of claim 31, further comprising an iodide salt.

33. The composition of claim 32, wherein the tertiary alcohol is a compound of formula (5)

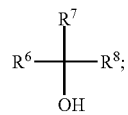

wherein $R^6$, $R^7$, and $R^8$ are each independently —(C$_1$-C$_6$) alkyl.

34. The composition of claim 33, wherein the tertiary alcohol is selected from the group consisting of tert-amyl alcohol, tert-butyl alcohol, 3-methyl-3-pentanol, 2,3-dimethyl-3-pentanol, 3-ethyl-3-pentanol, 2-methyl-2-hexanol, and mixtures of two or more thereof.

35. The composition of claim 34, wherein the tertiary alcohol is tert-amyl alcohol.

36. The composition of claim 31, wherein
the oxygen protecting group is selected from the group consisting of acetyl, benzoyl, benzyl, β-methoxyethoxymethyl, dimethoxytrityl, methoxymethyl, p-methoxybenzyl, methylthiomethyl, pivaloyl, tetrahydropyranyl, trityl, trimethylsilyl, tert-butyldimethylsilyl, tert-butyldimethylsilyloxymethyl, triisopropylsilyl, —C(O)O—CH$_2$—CH=CH$_2$), tert-butyl-diphenylsilyl, tert-butyl-dimethylsilyl, tri-iso-propylsilyl, [bis-(4-methoxyphenyl)phenylmethyl)], methoxymethyl, ethoxyethyl, triphenylmethyl, —C(O)(C$_1$-C$_6$)alkyl, —C(O)OR$^{18}$, and —(C$_1$-C$_6$)alkyl, each said alkyl being unsubstituted or substituted with 1, 2, 3, 4, or 5 independently-selected R$^{50}$ groups;
each R$^{18}$ is independently selected from —(C$_1$-C$_6$)alkyl, —(C$_2$-C$_6$)alkenyl, and —(C$_2$-C$_6$)alkynyl, each said alkyl, alkenyl, and alkynyl being unsubstituted or substituted with 1, 2, 3, 4, or 5 independently-selected R$^{50}$ groups; and each $R^{50}$ is independently selected from —Cl, —Br, —I, —NH$_2$, —CN, and phenyl.

37. The composition of claim 36, wherein $R^{16}$ is methylcyclopropyl, the ----- bond is a single bond, $R^9$ is —OH, and $R^{19}$ is —OCH$_3$.

* * * * *